(12) United States Patent
Gravel et al.

(10) Patent No.: US 6,703,197 B1
(45) Date of Patent: *Mar. 9, 2004

(54) HUMAN METHIONINE SYNTHASE: CLONING, AND METHODS FOR EVALUATING RISK OF NEURAL TUBE DEFECTS, CARDIOVASCULAR DISEASE, AND CANCER

(75) Inventors: Roy A. Gravel, Westmont (CA); Rima Rozen, Montreal West (CA); Daniel LeClerc, Montreal (CA); Philippe Goyette, Montreal (CA); Eric Campeau, Montreal (CA)

(73) Assignee: Martinex R&D, Inc., Montreal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 121 days.

(21) Appl. No.: 08/980,326

(22) Filed: Nov. 26, 1997

Related U.S. Application Data

(60) Provisional application No. 60/050,310, filed on Jun. 20, 1997, and provisional application No. 60/031,964, filed on Nov. 27, 1996.

(51) Int. Cl.[7] .................. C07H 21/02; C07H 21/04; C12Q 1/68
(52) U.S. Cl. .................. 435/6; 536/23.1; 536/23.5; 536/24.3; 536/24.31; 536/24.33
(58) Field of Search ................ 536/23.1, 23.5, 536/24.33, 24.31, 24.3; 435/6

(56) References Cited

PUBLICATIONS

Marra et al. (1996) GenBank Accession No. W33307, includes sequence alignment..*
Bannerjee et al. (1993) GenBank Accession No. J04975, includes sequence alignment.*
Li et al. GenBank Accession No. U75743, Jun. 1997.*
LeClerc et al. GenBank Accession No. U71285, Apr. 1997.*
Boushey, C.J., et al., *JAMA*, 274:1049–1057 (1995).
Chen, L.H. et al., *J. Biol. Chem.*, 272:3628–3634 (1997).
Chen, Z., et al., *J. Biol Chem.*, 269:27193–27197 (1994).
Drennan, C.L.., et al., *Science*, 266:1669–1674 (1994).
Fenton, W.A. and Rosenberg, L.E. *The Metabolic and Molecular Bases of Inherited Disease*, McGraw–Hill, New York, 3129–3149 (1995).
Fujii, K. and Huennekens, F.M., *J. Biol. Chem.*, 249:6745–6753 (1974).
Gulati, S. et al., *Hum. Molec. Genet.*, 5:1859–1865 (1996).
Li, Y.N., *Hum. Molec. Genet.*, 5:1851–1858 (1996).
Luschinky, C.L., et al., *J. Molec, Biol.*, 225:557–560 (1992).
Mellman, I.S., et al., *Proc. Nat'l. Acad. Sci. USA*, 76:405–409 (1979).
Mills, J.L., et al., *Lancet*, 345:149–151 (1995).
Rosenblatt, D.S., *The Metabolic and Molecular Bases of Inherited Disease*, McGraw–Hill, New York, 3111–3128 (1995).
Rosenblatt, D.S. et al., *J. Clin. Invest.*, 74:2149–2156 (1984).
Rozen, R., *Clin. Invst. Med.*, 19:171–178 (1996).
Schuh et al., *N. Engl. J. Med.*, 310:686–690 (1984).
Sillaots, S.L.., et al., *Biochem. Med. Metab. Biol.*, 47:242–249 (1992).
Steegers–Theunissen, R.P., et al., *Metab. Clin, Exp.*, 43:1475–1480 (1994).
Watkins, D. and Rosenblatt, D.S., *Am. J. Med. Genet.*, 34:427–434 (1989).
Watkins, D. and Rosenblatt, D.S., *J. Clin, Invest.*, 81:1690–1694 (1988).

* cited by examiner

*Primary Examiner*—Anne-Marie Falk
(74) *Attorney, Agent, or Firm*—Clark & Elbing, LLP; Kristina Bieker-Brady

(57) ABSTRACT

The invention features a method for detecting an increased likelihood of hyperhomocysteinemia and, in turn, an increased or decreased likelihood of neural tube defects or cardiovascular disease. The invention also features therapeutic methods for reducing the risk of neural tube defects, colon cancers and related cancers. Also provided are the sequences of the human methionine synthase gene and protein and compounds and kits for performing the methods of the invention.

6 Claims, 7 Drawing Sheets

FIG. 1

BOX 1:

```
            ** ***   *
Ec    (20)  DGGMGTMIQ    (SEQ ID NO: 3)
Ss    (20)  DGAMGTNLQ    (SEQ ID NO: 4)
Ml2    (5)  DGAMGTQLQ    (SEQ ID NO: 5)
Hi    (20)  DGAMGTMIQ    (SEQ ID NO: 6)
Ce    (22)  DGAMGTMIQ    (SEQ ID NO: 7)
Hs    (34)  DGGMGTMIQ    (SEQ ID NO: 8)
```

BOX 2:

```
            *************
Ec   (752)  ATVKGDVHDIGKN    (SEQ ID NO: 9)
Ss   (729)  ATVKGDVHDIGKN    (SEQ ID NO:10)
Ml2  (726)  ATVKGDVHDIGKN    (SEQ ID NO:11)
Hi   (142)  ATVKGDVHDIGKN    (SEQ ID NO:12)
Ce   (766)  ATVKGDVHDIGKN    (SEQ ID NO:13)
Hs   (778)  ATVKGDVHDIGKN    (SEQ ID NO:14)
```

BOX 3:

```
            ** **   *
Ec  (1095)  LAEAFAEYLH    (SEQ ID NO:15)
Ss  (1085)  MAEALAEWTH    (SEQ ID NO:16)
Ml1   (56)  LTEALAEYWH    (SEQ ID NO:17)
Hi   (490)  LAEAMAEYLH    (SEQ ID NO:18)
Ce  (1084)  LAEAYAEYLH    (SEQ ID NO:19)
Hs  (1133)  LAEAFAEELH    (SEQ ID NO:20)
```

BOX 4:

```
            *****  * **
Ec   (262)  GGCCGTTPQHI   (SEQ ID NO:21)
Ss   (243)  GGCCGTRPDHI   (SEQ ID NO:22)
Ml2  (226)  GGCCGTTPDHI   (SEQ ID NO:23)
Ce   (264)  GGCCGTTPDHI   (SEQ ID NO:24)
Hs   (321)  GGCCGSTPDHI   (SEQ ID NO:25)
```

FIG. 3: Methionine Synthase cDNA (SEQ ID NO: 1) and amino acid (SEQ ID NO: 2) sequences.

```
                                                    GGTCACCTGTGGAGAGCACGTCTTCTCTGCCGCGCCCTCTGCGCAAGGAGGAGACTCGACAAC
1    ATGTCACCCGCGCTCCAAGACCTGTCGCAACCCGAAGGTCTGAAGAAAACCCTGCGGGATGAGATCAATGCCATTCTGCAGAAGAGGATTATGGTGCTGGATGGAGGGATGGGGACCATG
     M  S  P  A  L  Q  D  L  S  Q  P  E  G  L  K  K  T  L  R  D  E  I  N  A  I  L  Q  K  R  I  M  V  L  D  G  G  M  G  T  M   40
121  ATCCAGCGGGAGAAGCTAAACGAAGAACACTTCCGAGGTCAGGAATTTAAAGATCATGCCAGGCCGCTGAAAGGCAACAATGACATTTTAAGTATAACTCAGCCTGATGTCATTTACCAA
     I  Q  R  E  K  L  N  E  E  H  F  R  G  Q  E  F  K  D  H  A  R  P  L  K  G  N  N  D  I  L  S  I  T  Q  P  D  V  I  Y  Q   80
241  ATCCATAAGGAATACTTGCTGGCTGGGGCAGATATCATTGAAACAAATACTTTTAGCAGCACTAGTATTGCCCAAGCTGACTATGGCCTTGAACACTTGGCCTACCGGATGAACATGTGC
     I  H  K  E  Y  L  L  A  G  A  D  I  I  E  T  N  T  F  S  S  T  S  I  A  Q  A  D  Y  G  L  E  H  L  A  Y  R  M  N  M  C   120
361  TCTGCAGGAGTGGCCAGAAAAGCTGCCGAGGAGGTAACTCTCCAGACAGGAATTAAGAGGTTTGTGGCAGGGGCTCTGGGTCCGACTAATAAGACACTCTCTGTGTCCCCATCTGTGGAA
     S  A  G  V  A  R  K  A  A  E  E  V  T  L  Q  T  G  I  K  R  F  V  A  G  A  L  G  P  T  N  K  T  L  S  V  S  P  S  V  E   160
481  AGGCCGGATTATAGGAACATCACATTTGATGAGCTTGTTGAAGCATACCAAGAGCAGGCCAAAGGACTTCTGGATGGCGGGGTTGATATCTTACTCATTGAAACTATTTTTGATACTGCC
     R  P  D  Y  R  N  I  T  F  D  E  L  V  E  A  Y  Q  E  Q  A  K  G  L  L  D  G  G  V  D  I  L  L  I  E  T  I  F  D  T  A   200
601  AATGCCAAGGCAGCCTTGTTTGCACTCCAAAATCTTTTTGAGGAGAAATATGCTCCCCGGCCTATCTTTATTTCAGGGACGATCGTTGATAAAAGTGGGCGGACTCTTTCCGGACAGACA
     N  A  K  A  A  L  F  A  L  Q  N  L  F  E  E  K  Y  A  P  R  P  I  F  I  S  G  T  I  V  D  K  S  G  R  T  L  S  G  Q  T   240
721  GGAGAGGGATTTGTCATCAGCGTGTCTCATGGAGAACCACTCTGCATTGGATTAAATTGTGCTTTGGGTGCAGCTGAGATGAGACCTTTTATTGAAATAATTGGAAAATGTACAACAGCC
     G  E  G  F  V  I  S  V  S  H  G  E  P  L  C  I  G  L  N  C  A  L  G  A  A  E  M  R  P  F  I  E  I  I  G  K  C  T  T  A   280
841  TATGTCCTCTGTTATCCCAATGCAGGTCTTCCCAACACCTTTGGTGACTATGATGAAACGCCTTCTATGATGGCCAAGCACCTAAAGGATTTTGCTATGGATGGCTTGGTCAATATAGTT
     Y  V  L  C  Y  P  N  A  G  L  P  N  T  F  G  D  Y  D  E  T  P  S  M  M  A  K  H  L  K  D  F  A  M  D  G  L  V  N  I  V   320
961  GGAGGATGCTGTGGGTCAACACCAGATCATATCAGGGAAATTGCTGAAGCTGTGAAAAATTGTAAGCCTAGAGTTCCACCTGCCACTGCTTTTGAAGGACATATGTTACTGTCTGGTCTA
     G  G  C  C  G  S  T  P  D  H  I  R  E  I  A  E  A  V  K  N  C  K  P  R  V  P  P  A  T  A  F  E  G  H  M  L  L  S  G  L   360
1081 GAGCCCTTCAGGATTGGACCGTACACCAACTTTGTTAACATTGGAGAGCGCTGTAATGTTGCAGGATCAAGGAAGTTTGCTAAACTCATCATGGCAGGAAACTATGAAGAAGCCTTGTGT
     E  P  F  R  I  G  P  Y  T  N  F  V  N  I  G  E  R  C  N  V  A  G  S  R  K  F  A  K  L  I  M  A  G  N  Y  E  E  A  L  C   400
1201 GTTGCCAAAGTGCAGGTGGAAATGGGAGCCCAGGTGTTGGATGTCAACATGGATGATGGCATGCTAGATGGTCCAAGTGCAATGACCAGATTTTGCAACTTAATTGCTTCCGAGCCAGAC
     V  A  K  V  Q  V  E  M  G  A  Q  V  L  D  V  N  M  D  D  G  M  L  D  G  P  S  A  M  T  R  F  C  N  L  I  A  S  E  P  D   440
1321 ATCGCAAAGGTACCTTTGTGCATCGACTCCTCCAATTTTGCTGTGATTGAAGCTGGGTTAAAGTGCTGCCAAGGGAAGTGCATTGTCAATAGCATTAGTCTGAAGGAAGGAGAGGACGAC
     I  A  K  V  P  L  C  I  D  S  S  N  F  A  V  I  E  A  G  L  K  C  C  Q  G  K  C  I  V  N  S  I  S  L  K  E  G  E  D  D   480
1441 TTCTTGGAGAAGGCCAGGAAGATTAAAAAGTATGGAGCTGCTATGGTGGTCATGGCTTTTGATGAAGAAGGACAGGCAACAGAAACAGACACAAAAATCAGAGTGTGCACCCGGGCCTAC
     F  L  E  K  A  R  K  I  K  K  Y  G  A  A  M  V  V  M  A  F  D  E  E  G  Q  A  T  E  T  D  T  K  I  R  V  C  T  R  A  Y   520
1561 CATCTGCTTGTGAAAAAACTGGGCTTTAATCCAAATGACATTATTTTTGACCCTAATATCCTAACCATTGGGACTGGAATGGAGGAACACAACTTGTATGCCATTAATTTTATCCATGCA
     H  L  L  V  K  K  L  G  F  N  P  N  D  I  I  F  D  P  N  I  L  T  I  G  T  G  M  E  E  H  N  L  Y  A  I  N  F  I  H  A   560
1681 ACAAAAGTCATTAAAGAAACATTACCTGGAGCCAGAATAAGTGGAGGTCTTTCCAACTTGTCCTTCTCCTTCCGAGGAATGGAAGCCATTCGAGAAGCAATGCATGGGGTTTTCCTTTAC
     T  K  V  I  K  E  T  L  P  G  A  R  I  S  G  G  L  S  N  L  S  F  S  F  R  G  M  E  A  I  R  E  A  M  H  G  V  F  L  Y   600
1801 CATGCAATCAAGTCTGGCATGGACATGGAGATAGTGAATGCTGGAAACCTCCCTGTGTATGATGATATCCATAAGGAACTTCTGCAGCTCTGTGAAGATCTCATCTGGAATAAAGACCCT
     H  A  I  K  S  G  M  D  M  E  I  V  N  A  G  N  L  P  V  Y  D  D  I  H  K  E  L  L  Q  L  C  E  D  L  I  W  N  K  D  P   640
1921 GAGGCCACTGAGAAGCTCTTACGTTATGCCCAGACTCAAGGCACAGGAGGGAAGAAAGTCATTCAGACTGATGAGTGGAGAAATGGCCCTGTCGAAGAACGCCTTGAGTATGCCCTTGTG
     E  A  T  E  K  L  L  R  Y  A  Q  T  Q  G  T  G  G  K  K  V  I  Q  T  D  E  W  R  N  G  P  V  E  E  R  L  E  Y  A  L  V   680
2041 AAGGGCATTGAAAAACATATTATTGAGGAAGCCAGGTTAAACCAAAAAAAATATCCCCGACCTCTCAATAATAATTGAAGGACCCCTGATGAATGGAATGAAAATTGTTGGT
     K  G  I  E  K  H  I  I  E  D  T  E  E  A  R  L  N  Q  K  K  Y  P  R  P  L  N  I  I  E  G  P  L  M  N  G  M  K  I  V  G   720
2161 GATCTTTTTGGAGCTGGAAAAATGTTTCTACCTCAGGTTATAAAGTCAGCCCGGGTTATGAAGAAGGCTGTTGGCCACCTTATCCCTTTCATGGAAAAAGAAAGAGAAGAAACCAGAGTG
     D  L  F  G  A  G  K  M  F  L  P  Q  V  I  K  S  A  R  V  M  K  K  A  V  G  H  L  I  P  F  M  E  K  E  R  E  E  T  R  V   760
2281 CTTAACGGCACAGTAGAAGAAGAGGACCCTTACCAGGGCACCATCGTGCTGGCCACTGTTAAAGGCGACGTGCACGACATAGGCAAGAACATAGTTGGAGTAGTCCTTGGCTGCAATAAT
     L  N  G  T  V  E  E  E  D  P  Y  Q  G  T  I  V  L  A  T  V  K  G  D  V  H  D  I  G  K  N  I  V  G  V  V  L  G  C  N  N   800
2401 TTCCGAGTTATTGATTTAGGAGTCATGACTCCATGTGATAAGATACTGAAAGCTGCTCTTGACCACAAAGCAGATATAATTGGCCTGTCAGGACTCATCACTCCTTCCCTGGATGAAATG
     F  R  V  I  D  L  G  V  M  T  P  C  D  K  I  L  K  A  A  L  D  H  K  A  D  I  I  G  L  S  G  L  I  T  P  S  L  D  E  M   840
2521 ATTTTTGTTGCCAAGGAAATGGAGAGATTAGCTATAAGGATTCCATTGTTGATTGAGGAGGAGCAACCACTTCAAAAACCCACACAGCAGTTAAAATAGCTCCGAGATACAGTGCACCTGTA
     I  F  V  A  K  E  M  E  R  L  A  I  R  I  P  L  L  I  G  G  A  T  T  S  K  T  H  T  A  V  K  I  A  P  R  Y  S  A  P  V   880
2641 ATCCATGTCCTGGACGCGTCCAAGAGTGTGGTGGTGTGTTCCCAGCTGTTAGATGAAAATCTAAAGGATGAATACTTTGAGGAAATCATGGAAGAATATGAAGATATTAGACAGGACCAT
     I  H  V  L  D  A  S  K  S  V  V  V  C  S  Q  L  L  D  E  N  L  K  D  E  Y  F  E  E  I  M  E  E  Y  E  D  I  R  Q  D  H   920
2761 TATGAGTCTCTCAAGGAGAGGGAGATACTTACCCTTAAGTCAAGCCAGAAAAAGTGGTTTCCAAATGGATTGGCTGTCTGAACCTCACCCAGTGAAGCCCACGTTTATTGGGACCCAGGTC
     Y  E  S  L  K  E  R  R  Y  L  P  L  S  Q  A  R  K  S  G  F  Q  M  D  W  L  S  E  P  H  P  V  K  P  T  F  I  G  T  Q  V   960
2881 TTTGAAGACTATGACCTGCAGAAGCTGGTGGACTACATTGACTGGAAGCCTTTCTTTGATGTCTGGCAGCTCCGGGGCAAGTACCCGAATCGAGGCTTCCCCAAGATATTTAACGACAAA
     F  E  D  Y  D  L  Q  K  L  V  D  Y  I  D  W  K  P  F  F  D  V  W  Q  L  R  G  K  Y  P  N  R  G  F  P  K  I  F  N  D  K   1000
3001 ACAGTAGGTGGAGAGGCCAGGAAGGTCTACGATGATGCCCACAATATGCTGAACACACTGATTAGTCAAAAGAAACTCCGGGCCCGGGGTGTGGTTGGGTTCTGGCCAGCACAGAGTATC
     T  V  G  G  E  A  R  K  V  Y  D  D  A  H  N  M  L  N  T  L  I  S  Q  K  K  L  R  A  R  G  V  V  G  F  W  P  A  Q  S  I   1040
3121 CAAGACGACATTCACCTGTACGCAGAGGCTGCTGTGCCCCAGGCTGCAGAGCCCATAGCCACTTTCTATGGGTTAAGGCAACAGGCTGAGAAGGACTCTGCCAGCACGGAGCCATACTAC
     Q  D  D  I  H  L  Y  A  E  A  A  V  P  Q  A  A  E  P  I  A  T  F  Y  G  L  R  Q  Q  A  E  K  D  S  A  S  T  E  P  Y  Y   1080
3241 TGCCTCTCAGACTTCATCGCTCCCTTGCATTCTGGCATCCGTGACTACCTGGGCCTGTTTGCCGTTGCCTGCTTTGGGGTAGAAGAGCTGAGCAAGGCCTATGAGGATGATGGTGACGAC
     C  L  S  D  F  I  A  P  L  H  S  G  I  R  D  Y  L  G  L  F  A  V  A  C  F  G  V  E  E  L  S  K  A  Y  E  D  D  G  D  D   1120
```

Fig. 3    2 of 2

```
3361 TACAGCAGCATCATGGTCAAGGCGCTGGGGGACCGGCTGGCAGAGGCCTTTGCAGAAGAGCTCCATGAAAGAGTTCGCCGAGAACTGTGGGCCTACTGTGGCAGTGAGCAGCTGGACGTC
      Y  S  S  I  M  V  K  A  L  G  D  R  L  A  E  A  F  A  E  E  L  H  E  R  V  R  R  E  L  W  A  Y  C  G  S  E  Q  L  D  V  1160
3481 GCAGACCTGCGAAGGTTGCGGTACAAGGGCATCCGCCCGGCTCCTGGCTACCCCAGCCAGCCCGACCACACCGAGAAGCTCACCATGTGGAGACTCGCAGACATCGAGCAGTCTACAGGC
      A  D  L  R  R  L  R  Y  K  G  I  R  P  A  P  G  Y  P  S  Q  P  D  H  T  E  K  L  T  M  W  R  L  A  D  I  E  Q  S  T  G  1200
3601 ATTAGGTTAACAGAATCATTAGCAATGGCACCTGCTTCAGCAGTCTCAGGCCTCTACTTCTCCAATTTGAAGTCCAAATATTTTGCTGTGGGGAAGATTTCCAAGGATCAGGTTGAGGAT
      I  R  L  T  E  S  L  A  M  A  P  A  S  A  V  S  G  L  Y  F  S  N  L  K  S  K  Y  F  A  V  G  K  I  S  K  D  Q  V  E  D  1240
3721 TATGCATTGAGGAAGAACATATCTGTGGCTGAGGTTGAGAAATGGCTTGGACCCATTTTGGGATATGATACAGACTAACTTTTTTTTTTTTTTTTGCCTTTTTTATCTTGATGATCCTCA
      Y  A  L  R  K  N  I  S  V  A  E  V  E  K  W  L  G  P  I  L  G  Y  D  T  D  -                                              1265
3841 AGGAAATACAACCTAG
```

FIG. 6

```
           box 2
     .***********.*  ...  *  ...**.  *  .*  ..  .      *
Ec   IATVKGDVHDIGKNIVGVVLQCNNYEIVDLGVMVPAEKILRTAKEVNADL
Hi   IATVKGDVHDIGKNIVSVVMQCNNFEVIDLGVMVPADKIIQTAINQKTDI
Ce   IATVKGDVHDIGKNIVSVVLGCNNFKVVDLGVMTPCENIIKAAIEEKADF
Ml   LATVKGDVHDIGKNLVDIILSNNGYEVVNLGIKQPITNILEVAEDKSADV
Ss   IATVKGDVHDIGKNLVDIILSNNGYRVVNLGIKQPVENIIEAYKKHRPDC
Mm   LATVKGDVHDIGKNIVGVVLACNNFRVIDLGVMTPCDKILQAALDHKADI
Hs   LATVKGDVHDIGKNIVGVVLGCNNFRVIDLGVMTPCDKILKAALDHKADI ...***.    *    *      ...    .  .*...***  ..      .   *
Ec   IGLSGLITPSLDEMVNVAKEMERQG--FTIPLLIGGATTSKAHTAVKIEQNY
Hi   IALSGLITPSLDEMEYFLGEMTRLG--LNLPVMIGGATTSKEHTAIKLYPKY
Ce   IGLSGLITPSLDEMVYVAKEMNRVG--LNIPLLIGGATTSKTHTAVKISPRY
Ml   VGMSGLLVKSTVIMKENLEEMNTRGVAEKFPVLLGGAALTRSYVENDLAEVY
Ss   IAMSGLLVKSTAFMKENLEVFNQEG--ITVPVILGGAALTPKFVHQDCQNTY
Mm   IGLSGLITPSLDEMIFVAKEMERLA--IKIPLLIGGATTSRTHTAVKIAPRY
Hs   IGLSGLITPSLDEMIFVAKEMERLA--IRIPLLIGGATTSKTHTAVKIAPRY
Mutations:             Δ
            .*   ..  ..     .            ..
Ec   -SGPTVYVQNASRTVGVVAALLSDTQR---DDFVARTRKEYETVRIQHGRKKP
Hi   KQHCVFYTSNASRAVTVCATLMNPEGR---AALWEQFKKDYEKIQQSFANSKP
Ce   -PHPVVHCLDASKSVVVCSSLSDMSVR---DAFLQDLNEDYEDVRQEHYASLK
Ml   -EGEVHYARDAFEGLKLMDTIMSAK-RARRCAGEPGVLSCRSRPQ
Ss   -KGQVIYGKDAFADLHFMDKLMPAKNSHNWDDF-QGFLGEYATE-NGHNVTTD
Mm   -SAPVIHVLDASKSVVVCSQLLDENLR---DDYLEEILEEYEDIRQDHYESLK
Hs   -SAPVIHVLDASKSVVVCSQLLDENLK---DEYFEEIMEEYEDIRQDHYESLK
Mutations:                                          GD
```

Ec (SEQ ID NO: 73)
Hi (SEQ ID NO: 72)
Ce (SEQ ID NO: 71)
Ml (SEQ ID NO: 70)
Ss (SEQ ID NO: 69)
Mm (SEQ ID NO: 68)
Hs (SEQ ID NO: 67)

HUMAN METHIONINE SYNTHASE: CLONING, AND METHODS FOR EVALUATING RISK OF NEURAL TUBE DEFECTS, CARDIOVASCULAR DISEASE, AND CANCER

CROSS REFERENCE TO RELATED APPLICATIONS

This invention claims priority from U.S. Provisional Applications Serial Nos. 60/031,964 and 60/050,310, filed Nov. 27, 1996 and Jun. 20, 1997, respectively.

FIELD OF THE INVENTION

The invention relates to the diagnosis and treatment of patients at risk for methionine synthase deficiency and associated altered risk for diseases such as neural tube defects, cardiovascular disease, and cancer.

BACKGROUND OF THE INVENTION

Methionine synthase (EC 2.1.1.13, 5-methyltetrahydrofolate-homocysteine methyltransferase) catalyses the remethylation of homocysteine to methionine in a reaction in which methylcobalamin serves as an intermediate methyl carrier. This occurs by transfer of the methyl group of 5-methyltetrahydrofolate to the enzyme-bound cob(I)alamin to form methylcobalamin with subsequent transfer of the methyl group to homocysteine to form methionine. Over time, cob(I)alamin may become oxidized to cob(II)alamin rendering the enzyme inactive. Regeneration of the functional enzyme occurs through the methionine synthase-mediated methylation of the cob(II)alamin in which S-adenosylmethionine is utilized as methyl donor. In *E. coli,* two flavodoxins have been implicated in the reductive activation of methionine synthase (Fujii, K. and Huennekens, F. M. (1974) *J. Biol. Chem.,* 249, 6745–6753). A methionine synthase-linked reducing system has yet to be identified in mammalian cells.

Deficiency of methionine synthase activity results in hyperhomocysteinemia, homocystinuria, and megaloblastic anemia without methylmalonic aciduria (Rosenblatt, D. S. (1995) *The Metabolic and Molecular Bases of Inherited Disease.* McGraw-Hill, New York, pp. 3111–3128; Fenton, W. A. and Rosenberg, L. E. (1995) *The Metabolic and Molecular Bases of Inherited Disease.* McGraw-Hill, New York, pp. 3129–3149). Two classes of methionine synthase-associated genetic diseases have been proposed based on complementation experiments between patient fibroblast cell lines (Watkins, D. and Rosenblatt, D. S. (1988) *J. Clin. Invest.,* 81, 1690–1694). One complementation group, cblE, has been postulated to be due to deficiency of the reducing system required for methionine synthesis (Rosenblatt, D. S., Cooper, B. A., Pottier, A., Lue-Shing, H., Matiaszuk, N. and Grauer, K. (1984) i J. Clin. Invest., 74, 2149–2156). Cells from patients in the cblE group fail to incorporate $^{14}$C-methyltetrahydrofolate into methionine in whole cells but have significant methionine synthase activity in cell extracts in the presence of a potent reducing agent. The second complementation group, cblG group, is thought to result from defects of the methionine synthase apoenzyme. Mutant cells from this group show deficient methionine synthase activity in both whole cells and cell extracts (Watkins, D. and Rosenblatt, D. S. (1988) *J. Clin. Invest.,* 81, 1690–1694; Watkins, D. and Rosenblatt, D. S. (1989) *Am. J. Med. Genet.,* 34, 427–434). Moreover, some cblG patients show defective binding of cobalamin to methionine synthase in cells incubated with radiolabelled cyanocobalamin (Sillaots, S. L., Hall, C. A., Hurteloup, V., and Rosenblatt, D. S. (1992) *Biochem. Med. Metab. Biol.,* 47, 242–249).

The cobalamin-dependent methionine synthase of *E. coli* has been crystallized and the structure of its active site determined (Luschinsky, C. L., Drummond, J. T., Matthews, R. G., and Ludwig, M. L. (1992) *J. Molec. Biol.,* 225, 557–560; Drennan, C. L., Huang, S., Drummond, J. T., Matthews, R. G., and Ludwig, M. L. (1994) *Science,* 266, 1669–1674.). The gene encoding methionine synthase has not been cloned from mammals.

SUMMARY OF THE INVENTION

We have cloned a gene for mammalian methionine synthase from humans and discovered that mutations in this gene are associated with hyperhomocysteinemia. Hyperhomocysteinemia is a condition that has been implicated in cardiovascular disease and neural tube defects. The presence of such mutations in methionine synthase gene are, thus, associated with increased risk for cardiovascular disease, altered risk for neural tube defects, and decreased risk of colon cancer. The invention features methods for risk detection and treatment of patients with hyperhomocysteinemia, cardiovascular disease, neural tube defects, and cancer. The invention also features compounds and kits which may be used to practice the methods of the invention, methods and compounds for treating or preventing these conditions and methods of identifying therapeutics for the treatment and prevention of these conditions.

In the first aspect, the invention provides purified wild-type mammalian methionine synthase gene, and mutated and polymorphic versions of the mammalian methionine synthase gene, fragments of the wild-type, mutated, and polymorphic gene, and sense and antisense sequences which may be used in the methods of the invention. Preferably, the gene is human. The proteins encoded therefrom are also an aspect of the invention as is a methionine synthase polypeptide having conservative substitutions. Preferably, the protein is a recombinant or purified protein having a mutation conferring hyperhomocysteinemia when present in a mammal. In addition, nucleic acids, including genomic DNA, mRNA, and cDNA, and the nucleic acid set forth in SEQ ID NO: 1, or degenerate variants thereof, are provided. The shorter nucleic acid sequences are appropriate for use in cloning, characterizing mutations, the construction of mutations, and creating deletions. In one embodiment, the nucleic acid set forth in SEQ ID NO: 1 is a probe that hybridizes at high stringency to sequences found within the nucleic acid of SEQ ID NO: 1. In further embodiments, the probe has a sequence complementary to at least 50% of at least 60 nucleotides, or the sequence is complementary to at least 90% of at least 18 nucleotides. Protein fragments also are provided. The shorter peptides may be used, for example, in the generation of antibodies to the methionine synthase protein. In some embodiments of this aspect of the invention nucleic acid fragments useful for detection of mutations in the region of the methionine synthase gene which encodes the cobalamin binding domain, and for detecting those mutations which indicate an increased likelihood of hyperhomocysteinemia, are preferred. Most preferred fragments are those useful for detecting the 2756 A→G, Δbp 2640–2642, and 2758 C→G mutations/polymorphisms. Given Applicants' discovery, one skilled in the art may readily determine which nucleic acids, detection methods, and mutations are most useful. Mutant proteins encoded by these mutations, including, but not limited to, H920D, ΔIle 881, and D919G are also provided by the invention (see, for example SEQ ID NOs: 74 and 75). Such mutant and polymorphic polypeptides may have decreased or increased biological activity, relative to wild-type methionine synthase.

In a related aspect, the invention provides antibodies that specifically bind mammalian methionine synthase, and a method for generating such an antibody. The antibody may specifically bind a wild-type methionine synthase, or a mutant or polymorphic methionine synthase. A method for detecting a wild-type, mutant, or polymorphic methionine synthase using the antibody is also provided by the invention.

In a second aspect, the invention provides a method for detecting an increased or decreased risk for hyperhomocysteinemia in a fetus or individual patient. Such a fetus or patient is at increased or decreased risk for neural tube defects and/or cardiovascular disease and at a decreased risk of developing colon cancer. The method includes detection of mutations in the methionine synthase gene present in the fetus, the individual patient, and/or the blood relatives of the fetus and patient. The presence of mutations, particularly in the cobalamin binding domain, indicate an altered (e.g., increased or decreased) risk of hyperhomocysteinemia, neural tube defects, cancer, and cardiovascular disease.

In a related aspect, the invention provides kits for the detection of mutations in the human methionine synthase gene. Such kits may include, for example, nucleic acid sequences, including probes, useful for PCR, SSCP, or RFLP detection of such mutations. Antibodies specific for proteins having mutations, correlated with an increased likelihood of hyperhomocysteinemia, may also be included in the kits of the invention.

In a fourth aspect, the invention features a method for screening for compounds which alter methionine synthase expression or ameliorate or exacerbate conditions of hyperhomocysteinemia. In various embodiments, the invention includes monitoring mutant or wild-type mammalian methionine synthase biological activity by monitoring methionine synthase enzymatic activity, or monitoring methionine synthase gene expression levels, by monitoring methionine synthase gene transcription, RNA stability, RNA translation and/or protein stability. In preferred embodiments the methionine synthase gene or protein being monitored is a gene or protein having a mutation associated with hyperhomocysteinemia, and samples are selected from purifed or partially purified methionine synthase, cell lysate, a cell, or an animal. Standard assay techniques known to those skilled in the art may be employed in the various embodiments. Compounds detected using this screen can be used to prevent or treat cardiovascular disease and neural tube defects or, in the alternative, to prevent or treat colon cancer. Kits for performing the above screens are also a part of the invention.

In a related aspect, the invention provides nucleic acids encoding wild-type, polymorphic, and mutated methionine synthase, in which the nucleic acid is operably linked to regulatory sequences, comprising a promoter, for the expression of the encoded polypeptides. In one embodiment, the promoter is inducible. The invention also provides cells, including prokaryotic and eukaryotic cells, comprising the nucleic acids. The eukaryotic cells may be yeast cells or mammalian cells.

In another related aspect, the invention features a transgenic mammal having a methionine synthase transgene. The gene may be wild-type, or may contain a mutation or polymorphism. The mammal may have a mutation associated with hyperhomocysteinemia in its methionine synthase gene in an expressible genetic construction or may have a deletion or knockout mutation in one or both alleles sufficient to abolish methionine synthase expression from the locus. In addition, or as a replacement, the mammal may have the methionine synthase gene from another species. For example, in one preferred embodiment the transgenic mammal is a rodent such as a mouse and the transgene is from a human. Cells from these transgenic or knockout animals are also provided by the invention. Such transgenic mammals may be used to screen for drugs for the treatment of diseases related to hyperhomocysteinemia.

In a sixth aspect, the invention features a method for treating patients with neural tube defects, colon cancer or related cancers by the delivery of antisense methionine synthase nucleic acid sufficient to lower the levels of methionine synthase polypeptide biological activity.

In a related aspect, the invention provides a method for treating or preventing cardiovascular disease, neural tube defects and cancer. The method comprises detecting an altered risk of such defects by analyzing methionine synthase nucleic acid, potential test subjects being a mammal, a potential parent, either male or female, a pregnant mammal, or a developing embryo or fetus, and then by exposing the subject (e.g., patient or pregnant mammal) to metabolites or cofactors such as, but not limited to, folate, cobalamin, S-adenosyl methionine, betaine, or methionine. In another related aspect, the invention features a method of pretreating or treating colon cancer or neural tube defects by inhibiting or activating methionine synthase biological activity in a mammal, pregnant mammal, embryo, or fetus. In preferred embodiments, this inhibiting or activating may be effected by exposing the subject to nucleic acids, peptides or small molecule-based inhibitors or activators of methionine synthase or substrates. The exposure is to quantities of the compound sufficient to reduce the probability of the subject developing the disease or to confer an increased likelihood of a decrease in the disease symptoms of the subject.

By "methionine synthase," "methionine synthase protein," or "methionine synthase polypeptide" is meant a polypeptide, or fragment thereof, which has at least 50% amino acid identity to boxes 1–4 of the human methionine synthase polypeptide (SEQ ID NO: 2) (see FIG. 1). It is understood that polypeptide products from splice variants of methionine synthase gene sequences are also included in this definition. Preferably, the methionine synthase protein is encoded by nucleic acid having a sequence which hybridizes to a nucleic acid sequence present in SEQ ID NO: 1 (human methionine synthase cDNA) under stringent conditions. Even more preferably the encoded polypeptide also has methionine synthase biological activity.

By "methionine synthase nucleic acid" or "methionine synthase gene" is meant a nucleic acid, such as genomic DNA, cDNA, or mRNA, that encodes methionine synthase, a methionine synthase protein, methionine synthase polypeptide, or portion thereof, as defined above. A methionine synthase nucleic acid also may be a methionine synthase primer or probe, or antisense nucleic acid that is complementary to a methionine synthase nucleic acid.

By "wild-type methionine synthase" is meant a methionine synthase nucleic acid or methionine synthase polypeptide having the nucleic acid and/or amino acid sequence most often observed among members of a given animal species and not statistically associated with a disease phenotype. Wild-type methionine synthase is biologically active methionine synthase. A wild-type methionine synthase is, for example, a human methionine synthase polypeptide having the sequence of SEQ ID NO: 1.

By "mutant methionine synthase," "methionine synthase mutation(s)," "mutations in methionine synthase," "polymorphic methionine synthase," "methionine synthase polymorphism(s)," "polymorphisms in methionine synthase," is meant a methionine synthase polypeptide or nucleic acid having a sequence that deviates from the wild-type sequence in a manner sufficient to confer an altered risk for a disease phenotype, or enhanced protection against a disease, in at least some genetic and/or environmental backgrounds. Such mutations may be naturally occurring or artificially induced. They may be, without limitation, insertion, deletion, frameshift, or missense mutations. A mutant methionine synthase protein may have one or more mutations, and such mutations may affect different aspects of methionine synthase biological activity (protein function), to various degrees. Alternatively, a methionine synthase mutation may indirectly affect methionine synthase biological activity by influencing, for example, the transcriptional activity of a gene encoding methionine synthase, or the stability of methionine synthase mRNA. For example, a mutant methionine synthase gene may be a gene which expresses a mutant methionine synthase protein or may be a gene which alters the level of methionine synthase protein in a manner sufficient to confer a disease phenotype in at least some genetic and/or environmental backgrounds.

By "biologically active" methionine synthase is meant a methionine synthase protein or methionine synthase gene that provides at least one biological function equivalent to that of the wild-type methionine synthase polypeptide or methionine synthase gene. Biological activities of a methionine synthase polypeptide include, and are not limited to, the ability to catalyze the methylation of homocysteine to generate methionine. Preferably, a biologically active methionine synthase will display activity equivalent to at least 35% of wild-type activity, more preferably, a biologically active methionine synthase will display at least 40–55% of wild-type activity, still more preferably, a biologically active methionine synthase will display at least 60–75% of wild-type activity, and most preferably, a biologically active methionine synthase will display at least 80–90% of wild-type activity. A biologically active methionine synthase also may display more than 100% of wild-type activity. Preferably, the biological activity of the wild-type methionine synthase is determined using the methionine synthase nucleic acid of SEQ ID NO: 1 or methionine synthase polypeptide of SEQ ID NO: 2. The degree of methionine synthase biological activity may be intrinsic to the methionine synthase polypeptide itself, or may be modulated by increasing or decreasing the number of methionine synthase polypeptide molecules present intracellularly.

By "high stringency conditions" is meant hybridization in 2×SSC at 40° C. with a DNA probe length of at least 40 nucleotides. For other definitions of high stringency conditions, see F. Ausubel et al., Current Protocols in Molecular Biology, pp. 6.3.1–6.3.6, John Wiley & Sons, New York, N.Y., 1994, hereby incorporated by reference.

By "analyzing" or "analysis" is meant subjecting a methionine synthase nucleic acid or methionine synthase polypeptide to a test procedure that allows the determination of whether a methionine synthase gene is wild-type or mutant. For example, one could analyze the methionine synthase genes of an animal by amplifying genomic DNA using the polymerase chain reaction, and then determining the DNA sequence of the amplified DNA.

By "probe" or "primer" is meant a single- or double-stranded DNA or RNA molecule of defined sequence that can base pair to a second DNA or RNA molecule that contains a complementary sequence (the "target"). The stability of the resulting hybrid depends upon the extent of the base pairing that occurs. The extent of base-pairing is affected by parameters such as the degree of complementarity between the probe and target molecules, and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for methionine synthase nucleic acid preferably will have at least 35% sequence identity, more preferably at least 45–55% sequence identity, still more preferably at least 60–75% sequence identity, still more preferably at least 80–90% sequence identity, and most preferably 100% sequence identity. Probes may be detectably-labelled, either radioactively, or non-radioactively, by methods well-known to those skilled in the art. Probes are used for methods involving nucleic acid hybridization, such as: nucleic acid sequencing, nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "pharmaceutically acceptable carrier" means a carrier which is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in Remington's Pharmaceutical Sciences, ($18^{th}$ edition), ed. A. Gennaro, 1990, Mack Publishing Company, Easton, Pa.

By "substantially identical" is meant a polypeptide or nucleic acid exhibiting at least 50%, preferably 85%, more preferably 90%, and most preferably 95% identity to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative nucleotide substitutions typically include substitutions which generate changes within the following groups: glycine, alanine, valine, isoleucine, leucine; aspartic acid, glutamic acid, asparagine, glutamine; serine, threonine; lysine, arginine; and phenylalanine, tyrosine.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is a methionine synthase polypeptide that is at least 75%, more preferably at least 90%, and most preferably at least 99%, by weight, pure. A substantially pure methionine synthase polypeptide may be obtained, for example, by extraction from a natural source (e.g., a fibroblast or liver cell) by expression of a recombinant nucleic acid encoding a methionine synthase polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides not only includes those derived from eukaryotic organisms but also those synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammals (e.g., rodents such as rats or mice) and the DNA (transgene) is inserted by artifice into the nuclear genome. Preferably the inserted DNA encodes a protein in at least some cells of the organism.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift mutation, or a missense mutation. Preferably, the mutation is an insertion or deletion, or is a frameshift mutation that creates a stop codon.

By "transformation" is meant any method for introducing foreign molecules into a cell. Lipofection, DEAE-dextran-mediated transfection, microinjection, protoplast fusion, calcium phosphate precipitation, retroviral delivery, electroporation, and biolistic transformation are just a few of the methods known to those skilled in the art which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "transformed cell" is meant a cell into which (or into an ancestor of which) has been introduced, by means of recombinant DNA techniques, a DNA molecule encoding (as used herein) a methionine synthase polypeptide.

By "positioned for expression" is meant that the DNA molecule is positioned adjacent to a DNA sequence which directs transcription and translation of the sequence (i.e., facilitates the production of, e.g., a methionine synthase polypeptide, a recombinant protein or a RNA molecule).

By "promoter" is meant a minimal sequence sufficient to direct transcription. Also included in the invention are those promoter elements which are sufficient to render promoter-dependent gene expression controllable for cell type-specific, tissue-specific, temporal-specific, or inducible by external signals or agents; such elements may be located in the 5' or 3' or intron sequence regions of the native gene.

By "operably linked" is meant that a gene and one or more regulatory sequences are connected in such a way as to permit gene expression when the appropriate molecules (e.g., transcriptional activator proteins) are bound to the regulatory sequences.

By "conserved region" is meant any stretch of six or more contiguous amino acids exhibiting at least 30%, preferably 50%, and most preferably 70% amino acid sequence identity between two or more of the methionine synthase family members, (e.g., between human and bacterial methionine synthase). Examples of conserved regions within methionine synthase are Boxes 1–4 (FIG. 1).

By "detectably-labeled" is meant any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as $^{32}P$ or $^{35}S$) and nonradioactive labeling (e.g., chemiluminescent labeling, e.g., fluorescein labeling).

By "antisense" as used herein in reference to nucleic acids, is meant a nucleic acid sequence that is complementary to the coding strand of a gene, preferably, a methionine synthase gene. An antisense nucleic acid is capable of preferentially lowering the activity of a mutant methionine synthase polypeptide encoded by a mutant methionine synthase gene.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., a methionine synthase amino-terminus-specific antibody. A purified antibody may be obtained, for example, by affinity chromatography using recombinantly-produced protein or conserved motif peptides and standard techniques.

By "specifically binds" is meant an antibody that recognizes and binds a human methionine synthase polypeptide but that does not substantially recognize and bind other non-methionine synthase molecules in a sample, e.g., a biological sample, that naturally includes protein. A preferred antibody binds to the methionine synthase polypeptide sequence of SEQ ID NO: 2 (FIG. 3).

By "neutralizing antibodies" is meant antibodies that interfere with any of the biological activities of a wild-type or mutant methionine synthase polypeptide, for example, the ability of methionine synthase to catalyze the transfer of a methyl group to homocysteine. The neutralizing antibody may reduce the ability of a methionine synthase polypeptide to catalyze the transfer preferably by 10% or more, more preferably by 25% or more, still more preferably by 50% or more, yet preferably by 70% or more, and most preferably by 90% or more. Any standard assay for the biological activity of methionine synthase, may be used to assess potentially neutralizing antibodies that are specific for methionine synthase.

By "expose" is meant to allow contact between an animal, cell, lysate or extract derived from a cell, or molecule derived from a cell, and a test compound.

By "treat" is meant to submit or subject an animal (e.g. a human), cell, lysate or extract derived from a cell, or molecule derived from a cell to a test compound.

By "test compound" is meant a chemical, be it naturally-occurring or artificially-derived, that is surveyed for its ability to modulate an alteration in reporter gene activity or protein levels, by employing one of the assay methods described herein. Test compounds may include, for example, peptides, polypeptides, synthesized organic molecules, naturally occurring organic molecules, nucleic acid molecules, and components thereof.

By "assaying" is meant analyzing the effect of a treatment, be it chemical or physical, administered to whole animals or cells derived therefrom. The material being analyzed may be an animal, a cell, a lysate or extract derived from a cell, or a molecule derived from a cell. The analysis may be for the purpose of detecting altered protein biological activity, altered protein stability, altered protein levels, altered gene expression, or altered RNA stability. The means for analyzing may include, for example, for example, the detection of the product of an enzymatic reaction, (e.g., the formation of methionine as a result of methionine synthase activity), antibody labeling, immunoprecipitation, and methods known to those skilled in the art for detecting nucleic acids.

By "modulating" is meant changing, either by decrease or increase, in biological activity.

By "a decrease" is meant a lowering in the level of biological activity, as measured by a lowering/increasing of: a) the formation of methionine as a result of methionine synthase activity; b) protein, as measured by ELISA; c) reporter gene activity, as measured by reporter gene assay, for example, lacZβ-galactosidase, green fluorescent protein, luciferase, etc.; or d) mRNA, levels of at least 30%, as measured by PCR relative to an internal control, for example, a "housekeeping" gene product such as β-actin or glyceraldehyde 3-phosphate dehydrogenase (GAPDH) or an externally added nucleic acid standard. In all cases, the lowering is preferably by at least 10% more preferably by at least 25%, still more preferably by at least 50%, and even more preferably by at least 70%.

By "an increase" is meant a rise in the level of biological activity, as measured by a lowering/increasing of: a) the formation of methionine as a result of methionine synthase activity; b) protein, as measured by ELISA; c) reporter gene activity, as measured by reporter gene assay, for example, lacZβ-galactosidase, green fluorescent protein, luciferase, etc.; or d) mRNA, levels of at least 30%, as measured by PCR relative to an internal control, for example, a "housekeeping" gene product such as β-actin or glyceraldehyde 3-phosphate dehydrogenase (GAPDH) or an externally added nucleic acid standard. Preferably, the increase is by 10% or more, more preferably by 25% or more, even more preferably by 2-fold, and most preferably by at least 3-fold.

By "alteration in the level of gene expression" is meant a change in gene activity such that the amount of a product of the gene, i.e., mRNA or polypeptide, is increased or decreased, or that the stability of the mRNA or the polypeptide is increased or decreased.

By "reporter gene" is meant any gene which encodes a product whose expression is detectable and/or quantitatable by immunological, chemical, biochemical or biological assays. A reporter gene product may, for example, have one of the following attributes, without restriction: fluorescence (e.g., green fluorescent protein), enzymatic activity (e.g., lacZβ-galactosidase, luciferase, chloramphenicol acetyltransferase), toxicity (e.g., ricin A), or an ability to be specifically bound by a second molecule (e.g., biotin or a detectably labelled antibody). It is understood that any engineered variants of reporter genes, which are readily available to one skilled in the art, are also included, without restriction, in the forgoing definition.

By "protein" or "polypeptide" or "polypeptide fragment" is meant any chain of more than two amino acids, regardless of post-translational modification (e.g., glycosylation or phosphorylation), constituting all or part of a naturally-occurring polypeptide or peptide, or constituting a non-naturally occurring polypeptide or peptide.

By "missense mutation" is meant the substitution of one purine or pyrimidine base (i.e. A, T, G, or C) by another within a nucleic acid sequence, such that the resulting new codon encodes an amino acid distinct from the amino acid originally encoded by the reference (e.g. wild-type) codon.

By "deletion mutation" is meant the deletion of at least one nucleotide within a polynucleotide coding sequence. A deletion mutation alters the reading frame of a coding region unless the deletion consists of one or more contiguous 3-nucleotide stretches (i.e. "codons"). Deletion of a codon from a nucleotide coding region results in the deletion of an amino acid from the resulting polypeptide.

By "frameshift mutation" is meant the insertion or deletion of at least one nucleotide within a polynucleotide coding sequence. A frameshift mutation alters the codon reading frame at and/or downstream from the mutation site. Such a mutation results either in the substitution of the encoded wild-type amino acid sequence by a novel amino acid sequence, or a premature termination of the encoded polypeptide due to the creation of a stop codon, or both.

DETAILED DESCRIPTION OF THE DRAWINGS

The drawings will first be briefly described.

FIG. 1 is a diagram showing four homologous regions among methionine synthases. Boxes 1 to 4 were used to design degenerate oligonucleotides for the initial cloning experiments. Ec: *Escherichia coli,* accession number J04975 (SEQ ID NOs: 3, 9, 15, and 21); Ss: Synechocystis sp., accession number D64002 (SEQ ID NOs: 4, 10, 16, and 22); Ml1 and Ml2: *Mycobacterium leprae,* accession number U000175 (see Drennan et al., 1994; SEQ ID NOs: 5, 11, 17, and 23); Hi: *Haemophilus influenzae,* accession number U32730 (SEQ ID NOs: 6, 12, and 18); Ce: *Caenorhabditis elegans,* accession number Z46828 (SEQ ID NOs: 7, 13, 19, and 24); Hs: *Homo sapiens,* this work (SEQ ID NOs: 8, 14, 20, and 25). Identical residues are indicated by a star above the alignment. Amino acid position for each protein is shown at left.

FIG. 2 is a diagram showing overlapping PCR fragments generated to clone human methionine synthase. Oligonucleotides are described in Table 1. Primers in parentheses designate mispriming outcomes that generated valid internal sequence. iPCRc: inverse PCR on cDNA, iPCRg: inverse PCR on genomic DNA.

FIG. 3 is a diagram showing nucleotide sequence (SEQ ID NO: 1) and deduced amino acid sequence (SEQ ID NO: 2) of human methionine synthase. The nucleotide residue numbering is shown in the left margin, and the amino acid residue numbering is shown in the right margin.

Figure 5C:
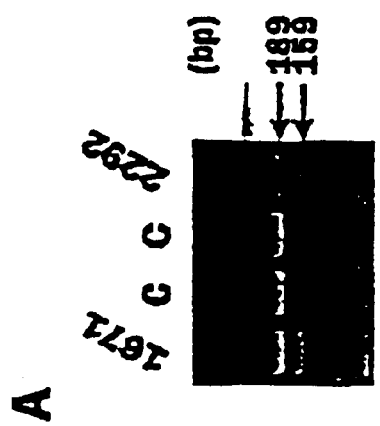
FIGS. 5A–5C is a series of photographs showing diagnostic tests for mutations in the methionine synthase gene. Numbers above the gel lanes correspond to patients cell lines whereas the letter "c" identifies wild-type controls.
Figure 5B:
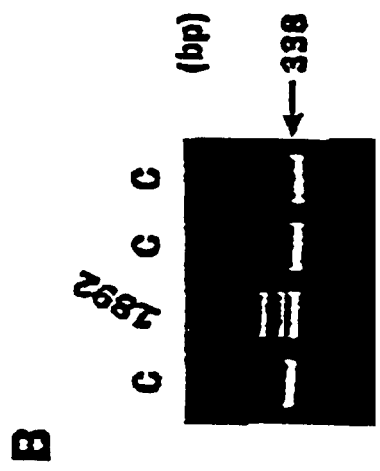
Figure 5A:
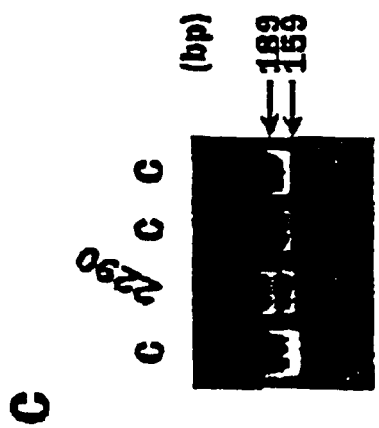

FIG. 5A: HaeIII restriction analysis of genomic DNA PCR products using primers #1796 and #305A. The 2756A→G change creates a HaeIII site. Expected fragments, 2756A allele: 189 bp, 2756G allele: 159 and 30 bp (the 30 bp fragment was run off the gel). FIG. 5B: Heteroduplex analysis of PCR products amplified from RT reactions of patient 1892 and 3 controls. RT-PCR was done with primers #1772 and #1773. Expected PCR product: 338bp, heteroduplexes can be seen above this band in patient 1892 (heterozygous for Δ2640–2642). C. Sau96I restriction analysis of genomic DNA PCR products. PCR was done as in (A). The 2758C→G mutation abolishes a Sau96I restriction endonuclease site in patient 2290. Expected fragments, control allele: 159, 30 bp, mutant allele: 189 bp (the 30 bp fragment has been run off the gel).

FIG. 6 shows an amino acid sequence comparison among methionine synthases in the Box 2 region. Identical residues are indicated by a star above the alignment. Dots show partially conserved residues, for which at least 6/7 identical or similar residues can be aligned (A,G,S,T; D,E,N,Q; V,L,I,M; K,R; and F,W,Y (Bordo, D. and Argos, P. (1991) *J Molec. Biol.*, 217, 721–729)). Mutations identified in this work are shown below the alignment. For abbreviations, see FIG. 1; Mm: *Mus musculus* (SEQ ID NOs: 67–73). The seven amino acids conserved in cobalamin-binding proteins (Drennan, C. L., Huang, S., Drummond, J. T., Matthews, R. G., and Ludwig, M. L. (1994) *Science*, 266, 1669–1674) are underlined.

DETAILED DESCRIPTION

We used specific regions of homology within the methionine synthase sequences of several lower organisms to clone a human methionine synthase cDNA (SEQ ID NO:1) by a combination of RT-PCR and inverse PCR. The enzyme (SEQ ID NO:2) is 1265 amino acids in length and contains the seven residue structure-based sequence fingerprint identified for cobalamin-containing enzymes. The gene was localized to chromosome 1q43 by the FISH technique. We have identified one missense mutation and a 3 base pair deletion in patients of the cblG complementation group of inherited homocysteine/folate disorders by SSCP and sequence analysis, as well as an amino acid substitution present in high frequency in the general population.

We conclude that the cDNA that we have identified corresponds to human methionine synthase on the basis of homology to known methionine synthases and by the identification of mutations in patients with a deficiency of enzyme activity. The most striking sequence conservation was found in four boxes of 9–13 amino acids. Box 2 has been proposed to correspond to part of the cobalamin binding domain (Drennan, C. L., Huang, S., Drummond, J. T., Matthews, R. G., and Ludwig, M. L. (1994) *Science*, 266, 1669–1674). It contains 13 consecutive residues that are identical in all known methionine synthases. Three amino acids within box 2 and four others C-terminal to it correspond to residues proposed by Drennan et al. (Drennan, C. L., Huang, S., Drummond, J. T., Matthews, R. G., and Ludwig, M. L. (1994) *Science*, 266, 1669–1674) as a structure-based sequence fingerprint for cobalamin binding. The three amino acids appear to make direct contact with the lower face of the corrin ring and dimethylbenzimidazole tail of cobalamin, determined from the crystal structure of the *E. coli* enzyme at 3 Å resolution (Drennan, C. L., Huang, S., Drummond, J. T., Matthews, R. G., and Ludwig, M. L. (1994) *Science*, 266, 1669–1674). All seven residues are identical in the human sequence (FIG. 6).

A survey of the NCBI databases for homology to the human methionine synthase using BLASTP yielded the various methionine synthases listed in FIG. 1, as well as the glutamate mutase (S41332, Q05488) and methylmalonyl-CoA mutase (P11653)(adenosyl-cobalamin dependent mutases) used to deduce the sequence fingerprint for cobalamin binding (Drennan, C. L., Huang, S., Drummond, J. T., Matthews, R. G., and Ludwig, M. L. (1994) *Science*, 266, 1669–1674). Homology was also found with the cobalamin binding region of the corrinoid: coenzyme M methyltransferase of *Methanosarcina barkeri* (U36337), the 5-methyltetrahydrofolate corrinoid/iron sulfur protein methyltransferase of *Clostridium thermoaceticum* (L34780) and the B12-dependent 2-methyleneglutarate mutase of *Clostridium barkeri* (S43552, S43237). Further, homology was found with the B12-binding site domain of the recently identified putative methionine synthase of *Agrobacterium tumefaciens* (U48718; partial N-terminal sequence is given, up to region of box 4). Significantly, homology with the B12-binding site domain was also found in the Hg resistance protein of *Myxococcus xanthus* (Z21955). This protein has not been described as having a cobalamin prosthetic group.

The two mutations we have identified as candidates for causing cblG disease are located in the vicinity of the cobalamin binding domain by comparison with *E. coli* methionine synthase (FIG. 6). Ile881 corresponds by sequence alignment to Val855 in the *E. coli* enzyme. Val855 is within a beta sheet strand that is part of an α/β domain that is a variant of the Rossmann nucleotide binding fold. The H920D substitution is found in a region which, in the *E. coli* enzyme, is in an α helix at the C-terminal end of the α/β domain. It is interesting that the polymorphism we have identified is at the adjacent residue (D919G). The functional role of the polymorphism and deleterious mutations will have to be examined in expression experiments to confirm their precise effect on the protein.

Through the cloning of a cDNA for human methionine synthase and mutations therein, we can now determine the properties of the human enzyme and complete the characterization of mutations in patients with severe synthase deficiency. This analysis has allowed us to tie mutations in the gene to disturbances in homocysteine metabolism which are known to result in hyperhomocysteinemia is a risk factor for cardiovascular disease (Boushey, C. J., Beresford, S. A., Omenn, G. S., and Motulsky, A. G. (1995) *JAMA*, 274, 1049–1057) and neural tube defects (Steegers-Theunissen, R. P., Boers, G. H., Trijbels, F. J., Finkelstein, J. D., Blom, H. J., Thomas, C. M., Borm, G. F., Wouters, M. G., and Eskes, T. K. (1994) *Metab. Clin. Exp.*, 43, 1475–1480; and Mills, J. L., McPartlin, J. M., Kirke, P. N., Lee, Y. J., Conley, M. R., Weir, D. G. and Scott, J. M. (1995) *Lancet*, 345, 149–151).

Our observations indicate the importance of methionine synthase as one of several genes involved in homocysteine metabolism. Results with other pathway genes underscores the significance of our findings. For example, a recently-identified mutation in methylenetetrahydrofolate reductase, the enzyme that synthesizes the 5-methyltetrahydrofolate substrate for the methionine synthase reaction, results in mild hyperhomocysteinemia (Frosst, P., Blom, H. J., Milos, R., Goyette, P., Sheppard, C. A., Matthews, R. G., Boers, G. J., den Heijer, M., Kluijtmans, L. A., van den Heuvel, L. P., et al. (1995) *Nat. Genet.,* 10, 111–113). Evidence is accumulating that this mutation, present in 35–40% of alleles, is a risk factor in both cardiovascular disease and neural tube defects (Rozen, R. (1996) *Clin. Invest. Med.,* 19, 171–178). We believe that genetic variants of methionine synthase similarly lead to mild hyperhomocysteinemia with consequent impact on these two multifactorial disorders.

We used specific regions of homology within the methionine synthase sequences, including a portion of the cobalamin binding site determined from the *E. coli* enzyme, to design degenerate oligonucleotides for RT-PCR-dependent cloning of human methionine synthase. We confirmed the identification of the cDNA sequences for human methionine synthase by the high degree of homology to the enzymes in other species and the identification of mutations in patients from the cblG complementation group. We also mapped the gene to human chromosome 1.

The assays described herein can be used to test for compounds that modulate methione synthase activity and hence may have therapeutic value in the prevention of neural tube defects, prevention and/or treatment of colon cancer, cardiovascular disease, hyperhomocysteinemia, and megaloblastic anemia without methylmalonic aciduria.

Screens for Compounds that Modulate Methionine Synthase Enzymatic Activity

Screens for potentially useful therapeutic compounds that modulate methionine synthase activity may be readily performed, for example, by assays that measure the incorporation of [14C]5-methyltetrahydrofolate into methionine or protein, or assays that measure the conversion of [14C]-homocysteine into methionine or protein. Examples of such assays, which employ whole cells or cell lysates, are well-known to those skilled in the art (see, e.g., Schuh, S., et al., *N. Engl. J. Med.* 1984, 310:686–69; Rosenblatt, D. S., et al., *J. Clin. Invest.* 1984, 74:2149–2156; Watkins, D., and Rosenblatt, D. S., *J. Clin. Invest.* 1988, 81:1690–1694; and Watkins, D., and Rosenblatt, D. S., *Am. J Med. Genet.* 1989, 34:427–434), and may be readily adapted for high throughput screening.

ELISA for the Detection of Compounds that Modulate Methionine Synthase Expression Enzyme-linked immunosorbant assays (ELISAs) are easily incorporated into high-throughput screens designed to test large numbers of compounds for their ability to modulate levels of a given protein. When used in the methods of the invention, changes in a given protein level of a sample, relative to a control, reflect changes in the methionine synthase expression status of the cells within the sample. Protocols for ELISA may be found, for example, in Ausubel et al., *Current Protocols in Molecular Biology,* John Wiley & Sons, New York, N.Y., 1997. Lysates from cells treated with potential modulators of methionine synthase expression are prepared (see, for example, Ausubel et al., supra), and are loaded onto the wells of microtiter plates coated with "capture" antibodies specific for methionine synthase. Unbound antigen is washed out, and a methionine synthase-specific antibody, coupled to an agent to allow for detection, is added. Agents allowing detection include alkaline phosphatase (which can be detected following addition of calorimetric substrates such as p-nitrophenolphosphate), horseradish peroxidase (which can be detected by chemiluminescent substrates such as ECL, commercially available from Amersham) or fluorescent compounds, such as FITC (which can be detected by fluorescence polarization or time-resolved fluorescence). The amount of antibody binding, and hence the level of a methionine synthase polypeptide within a lysate sample, is easily quantitated on a microtiter plate reader.

As a baseline control for methionine synthase expression, a sample that is not exposed to test compound is included. Housekeeping proteins are used as internal standards for absolute protein levels. A positive assay result, for example, identification of a compound that decreases methionine synthase expression, is indicated by a decrease in methionine synthase polypeptide within a sample, relative to the methionine synthase level observed in cells which are not treated with a test compound.

Reporter Gene Assays for Compounds that Modulate Methionine Synthase Expression

Assays employing the detection of reporter gene products are extremely sensitive and readily amenable to automation, hence making them ideal for the design of high-throughput screens. Assays for reporter genes may employ, for example, colorimetric, chemiluminescent, or fluorometric detection of reporter gene products. Many varieties of plasmid and viral vectors containing reporter gene cassettes are easily obtained. Such vectors contain cassettes encoding reporter genes such as lacZ/β-galactosidase, green fluorescent protein, and luciferase, among others. Cloned DNA fragments encoding transcriptional control regions of interest (e.g. that of the mammalian methionine synthase gene) are easily inserted, by DNA subcloning, into such reporter vectors, thereby placing a vector-encoded reporter gene under the transcriptional control of any gene promoter of interest. The transcriptional activity of a promoter operatively linked to a reporter gene can then be directly observed and quantitated as a function of reporter gene activity in a reporter gene assay.

Cells are transiently- or stably-transfected with methionine synthase control region/reporter gene constructs by methods that are well known to those skilled in the art. Transgenic mice containing methionine synthase control region/reporter gene constructs are used for late-stage screens in vivo. Cells containing methionine synthase/reporter gene constructs are exposed to compounds to be tested for their potential ability to modulate methionine synthase expression. At appropriate timepoints, cells are lysed and subjected to the appropriate reporter assays, for example, a calorimetric or chemiluminescent enzymatic assay for lacZ/β-galactosidase activity, or fluorescent detection of GFP. Changes in reporter gene activity of samples treated with test compounds, relative to reporter gene activity of appropriate control samples, indicate the presence of a compound that modulates methionine synthase expression.

Quantitative PCR of Methionine Synthase mRNA As an Assay for Compounds that Modulate Methionine Synthase Expression The polymerase chain reaction (PCR), when coupled to a preceding reverse transcription step (rtPCR), is a commonly used method for detecting vanishingly small quantities of a target mRNA. When performed within the linear range, with an appropriate internal control target (employing, for example, a housekeeping gene such as actin), such quantitative PCR provides an extremely precise and sensitive means of detecting slight modulations in mRNA levels. Moreover, this assay is easily performed in a 96-well format, and hence is easily incorporated into a high-throughput screening assay. Cells are treated with test compounds for the appropriate time course, lysed, the mRNA is reverse-transcribed, and the PCR is performed according to commonly used methods, (such as those described in Ausubel et al., *Current Protocols in Molecular Biology*, John Wiley & Sons, New York, N.Y., 1997), using oligonucleotide primers that specifically hybridize with methionine synthase nucleic acid. Changes in product levels of samples exposed to test compounds, relative to control samples, indicate test compounds that modulate methionine synthase expression.

Secondary Screens of Test Compounds that Appear to Modulate Methionine Synthase Activity After test compounds that appear to have methionine synthase-modulating activity are identified, it may be necessary or desirable to subject these compounds to further testing. At late stages testing will be performed in vivo to confirm that the compounds initially identified to affect methionine synthase activity will have the predicted effect in vivo.

Test Compounds

In general, novel drugs for prevention of neural tube defects, or prevention and/or treatment of colon cancer or cardiovascular disease are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their therapeutic activities for homocysteinemia, megaloblastic anemia without methylmalonic aciduria, cardiovasular disease, colon cancer, and neural tube defects should be employed whenever possible.

When a crude extract is found to modulate methionine synthase biological activity, further fractionation of the positive lead extract is necessary to isolate chemical constituents responsible for the observed effect. Thus, the goal of the extraction, fractionation, and purification process is the careful characterization and identification of a chemical entity within the crude extract that modulates methionine synthase biological activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using mammalian models of homocysteinemia, megaloblastic anemia without methylmalonic aciduria, cardiovasular disease, colon cancer, and neural tube defects.

Therapy

Compounds identified using any of the methods disclosed herein, may be administered to patients or experimental animals with a pharmaceutically-acceptable diluent, carrier, or excipient, in unit dosage form. Conventional pharmaceutical practice may be employed to provide suitable formulations or compositions to administer such compositions to patients or experimental animals. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for antagonists or agonists of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

EXAMPLES

The following examples are to illustrate, not limit the invention.

Example 1

Cloning Human Methionine Synthase cDNA

Figure 2:
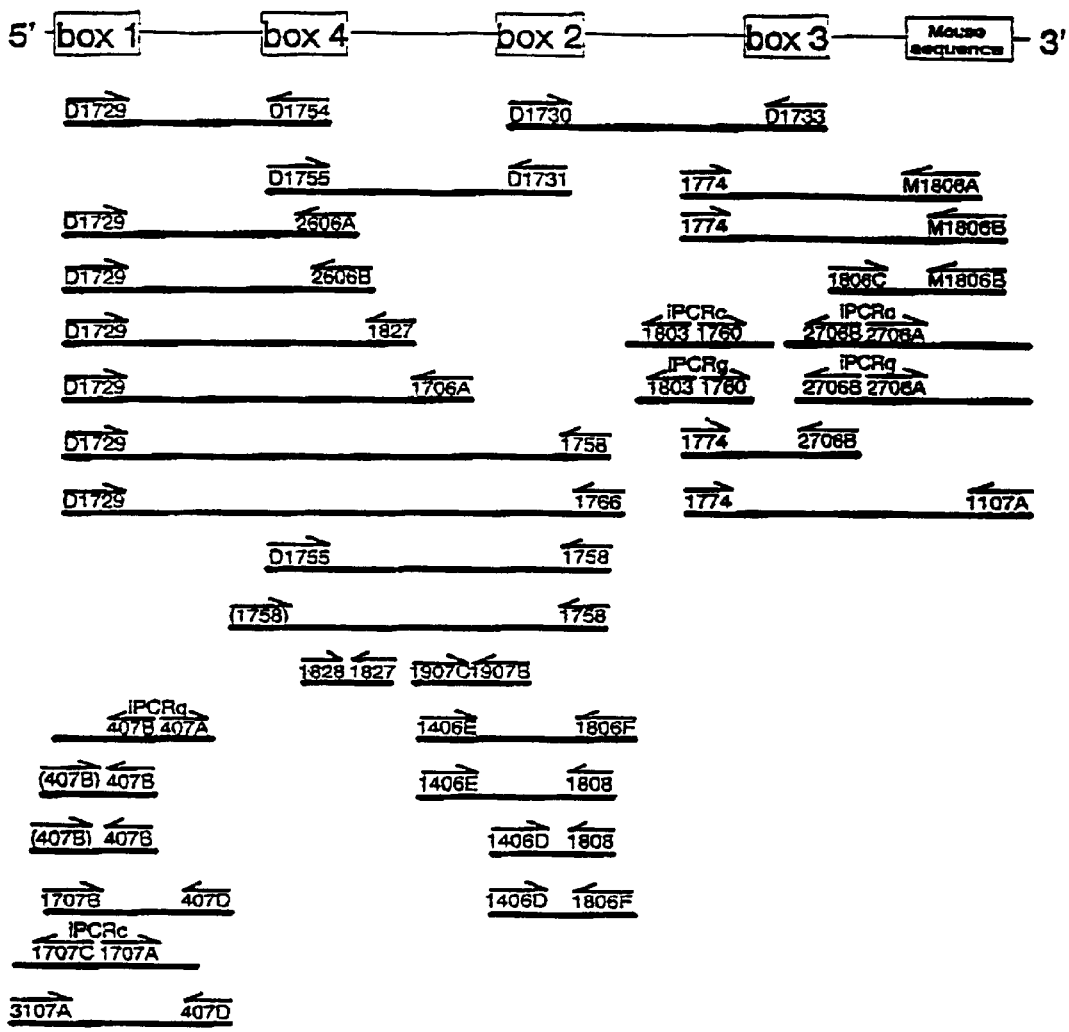

An initial survey of the NCBI databases yielded several sequences corresponding to methionine synthase from different organisms. Comparison of these sequences generated four very conserved regions identified as Boxes 1–4 in FIG. 1 (SEQ ID Nos:3–25). Degenerate oligonucleotides (SEQ ID Nos:26–66) were synthesized corresponding to these conserved sequences (Table 1). These were used as primers for RT-PCR with human and mouse mRNA. These experiments yielded PCR products which were subcloned, sequenced and aligned as shown in FIG. 2. In subsequent experiments, oligonucleotide primers were specified from the non-degenerate internal sequences of the subclones and additional PCR products encompassing the conserved boxes were obtained. In later experiments, additional sequences were obtained by inverse PCR ("PCR", FIG. 2) to obtain upstream or downstream sequences from those already determined. At the 3' end, a mouse sequence was obtained from the dbEST database (Accession Number W33307). This sequence was used as the source of primers for additional PCR experiments. Throughout the experiments, the sequences of the PCR products were considered provisionally authentic if they were homologous to the methionine synthase sequences obtained from the databases. The sequences were taken as error free by comparison of the sequences of at least two, and usually three, independent PCR reactions. Sequences were linked into a common sequence if RT-PCRs bridging independently isolated sequences were successful. Through this approach the complete coding sequence was determined through exclusive use of PCR reactions.

The coding sequence of human methionine synthase contains 3795 bp (SEQ ID NO:1) encoding a polypeptide of 1265 amino acids in length (SEQ ID NO:2) (FIG. 3), exceeding the length of published methionine synthases by 11–29 residues. The putative initiation codon is in a sequence of good context for the initiation of translation in eukaryotic cells (GACAACATGT, underlined. nucleotides matching Kozak consensus (SEQ ID NO: 76; Kozak, M. (1991) *J. Biol. Chem.*, 266, 19867–19870)). The predicted MW of methionine synthase is 141,000, comparing favorably with the published size of 151,000 based on SDS-polyacrylamide electrophoresis of the pig enzyme (Chen, Z., Crippen, K., Gulati, S., and Banerjee, R. (1994) *J. Biol. Chem.*, 269, 27193–27197). It shares 58% identity with the *E. coli* and 65% identity with the *C. elegans* enzyme.

Example 2

Chromosomal Location

Figure 4:
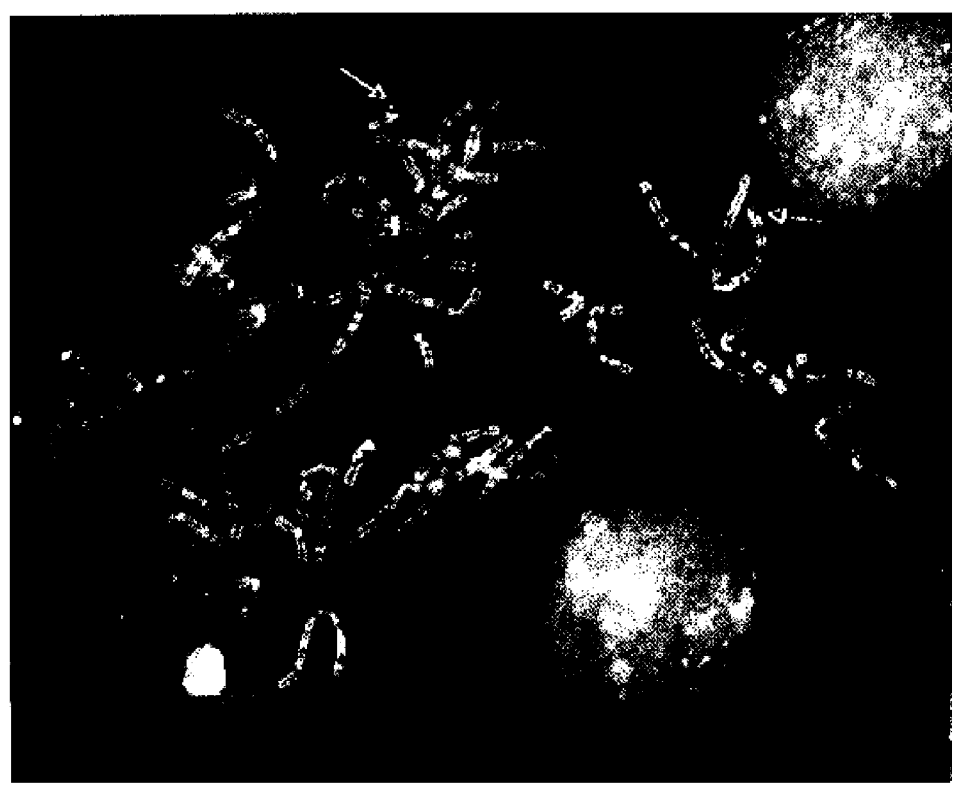
FIG. 4 is a photograph showing mapping of the human methionine synthase gene using FISH. Signals are clearly visible at 1q43 (arrows).

Using FISH, the gene encoding methionine synthase was mapped to chromosome band 1q43, close to the telomeric region of the long arm (FIG. 4). A total of 50 cells with at least one signal were observed. A signal was seen on 1 chromatid in 26 cells, on two chromatids in 14 cells, on 3 chromatids in 7 cells, and on 4 chromatids in 3 cells. These results confirm the previous assignment of the gene to chromosome 1 by Mellman et al. (Mellman, I. S., Lin, P. F., Ruddle, F. H., and Rosenberg, L. E. (1979) *Proc. Natl. Acad. Sci. USA*, 76, 405–409), who used cobalamin binding as a marker for the enzyme in human-hamster hybrids. cl Example 3

Mutations in the cblG Complementation Group

Patients with deficiency of methionine synthase activity have been grouped into the cblG complementation group in cell fusion experiments (Watkins, D. and Rosenblatt, D. S. (1988) *J. Clin. Invest.*, 81, 1690–1694). Fibroblast cultures from patients assigned to cblG were examined by RT-PCR based SSCP analysis. Three mutations were identified by sequencing PCR fragments showing band shifts by SSCP (FIG. 5). In each case, the change was confirmed by an independent diagnostic test on genomic DNA or a separate preparation of cDNA from patient fibroblasts. One of the mutations, 2756A→G (D919G), was confirmed by a diagnostic test that monitored the presence of a HaeIII site created by the mutation (FIG. 5A). Using this test, it was identified as a polymorphism since it was seen in 8 of 52 control alleles (15%). In two other cases, candidate deleterious mutations were identified. One is a 3 bp deletion, bp 2640–2642, that results in the deletion of an isoleucine codon (ΔIle881). It was confirmed by heteroduplex analysis of cDNA generated by RT-PCR (FIG. 5B). The second is a point mutation, 2758C→G. It results in the amino acid substitution H920D. It was confirmed in genomic DNA by the loss of a Sau96I site (FIG. 5C). The latter two mutations were heterozygous in the patient cell lines. Their second mutation has not been identified. The candidate deleterious mutations were not seen in panels of 68 or 52 control alleles, respectively.

Example 4

Additional Roles for Methionine Synthase Polymorphism (Asp919Gly or D919G) in Disease The following data suggest that the D919G polymorphism contributes to altered metabolism of homocysteine, methionine, folates, Vit. B12, and S-adenosylmethionine.

First in a Montreal study (n=303), in which mother-child pairs (cases and controls) were examined, we observed that infants who were homozygous for the polymorphism (Gly/Gly; Table 2) were at decreased risk for NTD. Measurements of serum folate, RBC folate, plasma homocysteine and serum cobalamin did not give any statistically significant differences, except the trend was toward low folate levels in Gly/Gly individuals (cases and controls).

A second study (n=255) in California also examined the methionine synthase polymorphism as a risk factor for neural tube defects (Table 3). This study shows a similar decreased risk of neural tube defects in children homozygous for Gly/Gly. Since the study encompassed a mix of whites and Hispanics, the data were reexamined stratified according to ethnic origin. Both groups showed a protective effect of Gly/Gly.

In summary, two independent studies suggest a protective effect of Gly/Gly against the risk of neural tube defects. This is likely to be mediated by a mild reduction in methionine synthase activity.

Next, in a study of colon cancer, (212 cases and 345 controls), we observed a decreased risk for colon cancer in the individuals who were homozygous for the polymorphism (relative risk=0.62); see Table 4. In the same study, we observed significantly decreased levels of plasma folate in individuals who were homozygous for the polymorphism; see Table 5.

The Boston study described in Tables 4 and 5 is presented again in Table 6 with the data stratified according to alcohol intake. As shown in the table, Gly/Gly individuals with a low to medium alcohol intake had a relative risk associated with colon cancer of 0.1 1. The combined data (low+high alcohol) gave a risk level of 0.62 (Table 6).

In summary, drug therapy targeted to a reduction in methionine synthase activity may be protective in individuals at risk for colon cancer or at risk for neural tube defects. Additional polymorphisms or mutations may also exert a protective effect against the risk of neural tube defects or colon cancer. Conversely, it is understood that some polymorphisms and/or mutations may enhance the risk of neural tube defects or colon cancer, for example, by increasing methionine synthase activity.

Example 5

Role of Polymorphism on Homocysteine and Folate Levels

Third, in a study of individuals participating in the U.S. NHLBI Family Heart Study, we observed both an increase in plasma homocysteine following a methionine load and a decrease in plasma folate in individuals who were homozygous for this polymorphism; see Table 7.

Example 6

Methionine Synthase Assays for the Detection of Compounds that Modulate Methionine Synthase Activity and Expression Potentially useful therapeutic compounds that modulate (e.g. increase or decrease) methionine synthase activity or expression may be isolated by various screens that are well-known to those skilled in the art. Such compounds may modulate methionine synthase expression at the pre- or post-transcriptional level, or at the pre- or post-translational level.

Example 7

Materials and Methods

Cell lines.

The skin fibroblast lines are from patients with methionine synthase deficiency. They were assigned to the cblG complementation group in cell fusion experiments assayed by $^{14}$C-methyltetrahydrofolate incorporation into cellular macromolecules (Watkins, D. and Rosenblatt, D. S. (1988) *J. Clin. Invest.*, 81, 1690–1694). Control fibroblasts were from other laboratory stocks or the Montreal Children's Hospital Cell Repository for Mutant Human Cell Strains. Of the patients for which non-polymorphic mutations were found, WG 1892, a Caucasian male, was diagnosed at the age of 4 years with developmental delay, tremors, gait instability, megaloblastic anemia and homocystinuria; and WG2290, also a Caucasian male, was diagnosed at age 3 months with failure to thrive, severe eczema, megaloblastic anemia and surprisingly both homocystinuria and methylmalonic aciduria.

Materials.

The T/A cloning kit was from Invitrogen. The Geneclean III Kit was obtained from Bio 101 Inc. and the Wizard Mini-Preps were from Promega. The random-primed DNA labelling kit was from Boehringer-Mannheim. Taq polymerase, Superscript II reverse transcriptase, AMV reverse transcriptase, Trizol reagent, DNAzol reagent, T4 DNA ligase, and restriction enzymes were purchased from Gibco BRL. The Sequenase kit for manual sequencing was from United States Biochemicals. The α-[$^{35}$S]dATP (12.5 Ci/mole) was from Dupont or ICN. The oligonucleotide primers were synthesized by R. Clarizio of the Montreal Children's Hospital Research Institute Oligonucleotide Synthesis Facility or the Sheldon Biotechnology Centre, McGill University.

Homology matches.

Comparisons were made between the published *E. coli* cobalamin-dependent methionine synthase sequence and sequences in the NCBI databases (dbEST and GenBank) using the BLAST programs.

PCR cloning and DNA sequencing.

DNA was prepared from fibroblast pellets by the method of Hoar et al. (Hoar, D. I., Haslam, D. B., and Starozik, D. M. (1984) *Prenat. Diag.*, 4, 241–247). Total cellular RNA was isolated by the method of Chirgwin et al. (Chirgwin, J. M., Przybyla, A. E., MacDonald, R. J., and Rutter, W. J. (1979) *Biochemistry*, 18, 5294–5299) and reverse-transcribed using oligo-dT$_{15}$ as primer. PCR was conducted using degenerate oligonucleotides as primers, paired so as to link the sequences of different homology boxes. The PCRs were conducted as described previously (Triggs-Raine, B. L., Akerman, B. R., Clarke, J. T., and Gravel, R. A. (1991) *Am. J. Hum. Genet.*, 49, 1041–1054) except that the temperature of incubation was modified to accommodate the use of reduced temperatures in the annealing step or by step-down PCR (Hecker, K. H. and Roux, K. H. (1996) *Biotechniques*, 20, 478–485.(Abstract)). In some experiments, inverse PCR was used to determine sequence upstream or downstream of known sequence (Ochman, H., Medhora, M. M., Garza, D., and Hartl, D. L. (1990) *PCR Protocols: A Guide to Methods and Applications*, Academic Press, San Diego, pp. 219–227). In these instances, genomic DNA or cDNA prepared by reverse transcription of RNA was digested with different four base restriction endonucleases, ligated with T4 DNA ligase, and amplified by PCR using adjacent oligonucleotides priming in opposite directions. Templates for inverse PCR at the cDNA level were generated with 12.5 μg RNA reversed transcribed using AMV-RT. Second strand synthesis was carried out using the random-primed DNA labelling kit adding 1 μl of each dNTP. Samples were incubated 30 min. at 37° C. Template was then treated as genomic DNA for digestion and ligation. Inverse PCR was used to obtain the 5' and 3' ends of the cDNA and to define an intron sequence adjacent to a splice junction for the design of a mutation diagnostic test. The PCR products were purified with Geneclean and were subcloned in the pCR2.1 vector and transformed into *E. coli* as per the supplier's protocol (TA Cloning Kit). The candidate clones were sequenced manually or by the DNA Core Facility of the Canadian Genetic Diseases Network or the McGill University Sheldon Biotechnology Centre.

Mutation analysis.

Genomic DNA and RNA were isolated from control or patient fibroblast pellets using the DNAzol or Trizol reagents, respectively, as per the manufacturer. The cDNA template for PCR was prepared by reverse transcription of 3–5 ug total RNA in reactions containing 400 U of Superscript II reverse transcriptase and 100 ng random hexamers in a total reaction volume of 20 ul. SSCP analysis was performed as described previously (Triggs-Raine, B. L., Akerman, B. R., Clarke, J. T., and Gravel, R. A. (1991) *Am. J. Hum. Genet.*, 49, 1041–1054) in reactions containing 4 μl of template, 1 μl of each dTTP, dCTP, dGTP (0.625 mM), 0.5 μl of dATP (0.625 mM), 1 μl α-[$^{35}$S]-dATP (12.5 Ci/mole). The radio labelled PCR products mixed with sequencing stop solution were heat denatured and quick chilled on ice prior to loading (Triggs-Raine, B. L., Akerman, B. R., Clarke, J. T., and Gravel, R. A. (1991) *Am. J. Hum. Genet.*, 49, 1041–1054). As well, an aliquot of each sample was run without prior heating to identify the duplex product. The fragments were subjected to electrophoresis in a 6% acrylamide/10% glycerol gel in 1×TBE for 18 hrs at 8 watts at room temperature. The gel was dried and exposed to Biomax film (Kodak). Fragments that displayed band shifts were sequenced directly.

Two mutations were confirmed directly in PCR amplification products from genomic DNA and one mutation was confirmed in reversed transcribed mRNA. The PCR reactions for mutation confirmation were performed using 4 μl of cDNA template or 500 ng genomic DNA, 500 ng of specific primers, 2.5 U Taq polymerase and 1.5 mM MgCl2 in a 50 μl volume. Heteroduplex analysis was accomplished by preheating PCR products to 95° C. for five minutes and subjecting the samples to electrophoresis in a 9% polyacrylamide gel (Triggs-Raine, B. L., Akerman, B. R., Clarke, J. T., and Gravel, R. A. (1991) *Am. J. Hum. Genet.*, 49, 1041–1054). Other diagnostic assays were accomplished by digesting a 15 μl sample of the PCR products with the indicated restriction endonuclease prior to electrophoresis.

Chromosomal localization.

Human metaphase spreads were obtained from short-term cultures of phytohemaglutinin-stimulated peripheral blood lymphocytes. The cells were synchronized with thymidine and treated with BrdU during the late S-phase before harvesting for simultaneous observation of the hybridized sites and chromosome banding. The protocol for FISH was essentially as described previously (Lemieux, N., Malfoy, B., and Forrest, G. L. (1993) *Genomics*, 15, 169–172; Zhang, X. X., Rozen, R., Hediger, M. A., Goodyer, P., and Eydoux, P. (1994) *Genomics*, 24, 413–414). Briefly, a 5 kb DNA fragment of the methionine synthase genomic DNA (generated by PCR using oligonucleotides #1782 and #1780) was labelled by nick translation with biotin-16-dUTP (Boehringer-Mannheim), ethanol precipitated and dissolved in hybridization buffer at a final concentration of 8 ng/μl. The slides were denatured in 70% formamide, 2×SSC at 70° C. for 2 min. The biotinylated probe was denatured in the hybridization buffer at 95° C. for 10 min, quickly cooled on ice, then applied on slides. Post-washing was done by rinsing in 50% formamide, 2×SSC at 37° C. The slides were incubated with rabbit antibiotin antibody (Enzo Biochemicals), biotinylated goat anti-rabbit antibodies (BRL) and streptavidin-FITC. They were stained with propidium iodide and mounted in p-phenylenediamine, pH 11. Cells were observed under the microscope (Zeiss), then captured through a CCD camera and processed using a FISH software (Applied Imaging).

TABLE 1

Oligonucleotides used for cDNA cloning, chromosome mapping and mutation detection.

| Oligonucleotide[a] | Sequence | Location[b] |
|---|---|---|
| D1729 | (SEQ ID NO:26) 5'-GAYGGNGCNATGGGNACNATGATHCA | 100–125 |
| D1730 | (SEQ ID NO:27) 5'-GCNACNGTNAARGGNGAYGTNCAYGAYAT | 2332–2360 |
| D1731 | (SEQ ID NO:28) 5'-RTTYTTNCCDATRTCRTGNACRTCNCCYTT | 2370–2341 |
| D1733 | (SEQ ID NO:29) 5'-RTGNAGRTAYTCNGCRAANGCYTCNGC | 3426–3400 |
| D1754 | (SEQ ID NO:30) 5'-ATRTGRTCNGGNGTNGTNCCRCARCANCCNCC | 992–961 |
| D1755 | (SEQ ID NO:31) 5'-GGNGGNTGYTGYGGNACNACNCCNGAYCAYAT | 961–992 |
| M1806A | (SEQ ID NO:32) 5'-GTCTGTGTCATAGCCCAGAATGGG | 3795–3772 |
| M1806B | (SEQ ID NO:33) 5'-TCAGTCTGTGTCATAGCCCAGAAT | 3798–3775 |
| 305A | (SEQ ID NO:34) 5'-GAACTAGAAGACAGAAATTCTCTA | (intronic) |
| 407A | (SEQ ID NO:35) 5'-TTCCGAGGTCAGGAATTTAAAGATCA | 151–176 |
| 407B | (SEQ ID NO:36) 5'-GTGTTCTTCGTTTAGCTTCTCCCG | 150–127 |
| 407D | (SEQ ID NO:37) 5'-CCCCAGCCAGCAAGTATTCCTTAT | 268–245 |
| 1107A | (SEQ ID NO:38) 5'-CTAGGTTGTATTTCCTTGAGGATC | 3856–3833 |
| 1406D | (SEQ ID NO:39) 5'-GGAGCTGGAAAAATGTTTCTACCTC | 2170–2194 |
| 1406E | (SEQ ID NO:40) 5'-ACAGGAGGGAAGAAAGTCATTCAG | 1963–1986 |
| 1706A | (SEQ ID NO:41) 5'-CCTTCAATTATATTGAGAGGTCGGG | 2129–2105 |
| 1707A | (SEQ ID NO:42) 5'-CAACCCGAAGGTCTGAAGAAAACC | 28–51 |
| 1707B | (SEQ ID NO:43) 5'-CCCGCGCTCCAAGACCTGTCG | 7–27 |
| 1707C | (SEQ ID NO:44) 5'-CGACAGGTCTTGGAGCGCGGG | 27–7 |
| 1758 | (SEQ ID NO:45) 5'-GGAGTCATGACTCCTAAATCAATAACTC | 2432–2405 |
| 1760 | (SEQ ID NO:46) 5'-GACGACTACAGCAGCATCATGGT | 3355–3377 |
| 1766 | (SEQ ID NO:47) 5'-AAAAATCATTTCATCCAGGGAA | 2526–2505 |
| 1772 | (SEQ ID NO:48) 5'-ATAGGCAAGAACATAGTTGGAGTAGT | 2359–2384 |
| 1773 | (SEQ ID NO:49) 5'-TTTCATCTAACAGCTGGGAACACAC | 2698–2674 |
| 1774 | (SEQ ID NO:50) 5'-TGCCTCTCAGACTTCATCGCTCCC | 3241–3264 |
| 1780 | (SEQ ID NO:51) 5'-TGCAGCCTGGGGCACAGCAGC | 3168–3148 |
| 1782 | (SEQ ID NO:52) 5'-ATGGATTGGCTGTCTGAACCTCAC | 2824–2847 |
| 1796 | (SEQ ID NO:53) 5'-CATGGAAGAATATGAAGATATTAGAC | 2727–2752 |
| 1803 | (SEQ ID NO:54) 5'-ACCATCATCCTCATAGGCCTTGCT | 3354–3331 |
| 1806C | (SEQ ID NO:55) 5'-CAGACCTGCGAAGGTTGCGGTAC | 3482–3504 |
| 1806F | (SEQ ID NO:56) 5'-GAAGTGGTTGCTCCTCCAATCAAC | 2591–2568 |
| 1808 | (SEQ ID NO:57) 5'-GAGCAGCTTTCAGTATCTTATCACAT | 2458–2433 |
| 1827 | (SEQ ID NO:58) 5'-ACAAGTTGTGTTCCTCCATTCCAGT | 1657–1633 |
| 1828 | (SEQ ID NO:59) 5'-AGAGCGCTGTAATGTTGCAGGATCA | 1125–1149 |
| 1907B | (SEQ ID NO:60) 5'-TGTTTTTCAATGCCCTTCACAAGGG | 2057–2033 |
| 1907C | (SEQ ID NO:61) 5'-TAAAAAGTATGGAGCTGCTATGGTG | 1464–1488 |
| 2606A | (SEQ ID NO:62) 5'-GACCAGACAGTAACATATGTCCTTC | 1078–1054 |
| 2606B | (SEQ ID NO:63) 5'-ACATTACAGCGCTCTCCAATGTTAAC | 1139–1114 |
| 2706A | (SEQ ID NO:64) 5'-TGAGGTTGAGAAATGGCTTGGACC | 3750–3773 |
| 2706B | (SEQ ID NO:65) 5'-GCCACAGATATGTTCTTCCTCAATG | 3749–3725 |
| 3107A | (SEQ ID NO:66) 5'-TGTGGAGAGCACGTCTTCTCTGCC | -55 —32 |

[a]Numbers with the prefix "D" refer to oligonucleotides with degenerate bases shown as N (any base), H (A, C, or T), D (A, G, or T), Y (T or C), or R (A or G); those with the prefix "M" refer to mouse sequences (see FIG. 3).
[b]From the first methionine codon, see FIG. 3.

TABLE 2

MS Polymorphism in Neural Tube Defects - Montreal Study

| Genotype | Cases N | Cases % | Case mothers N | Case mothers % | Controls N | Controls % | Control mothers N | Control mothers % | Odds ratio* | 95% C.I. |
|---|---|---|---|---|---|---|---|---|---|---|
| Asp/Asp | 38 | 69 | 40 | 66 | 59 | 61 | 55 | 61 | | |
| Asp/Gly | 17 | 31 | 20 | 33 | 28 | 29 | 34 | 38 | | |
| Gly/Gly | 0 | 0.9 | 1 | 2 | 10 | 10 | 1 | 1 | 0.07 | 0.004–1.29 |
| N | 55 | | 61 | | 97 | | 90 | | | |

*Odds ratio calculated for genotypes Asp/Asp vs Gly/Gly
(to permit the calculation, the 0 cell was increased to 0.5)

TABLE 3

MS Polymorphisms in Neural Tube Defects - California Study

| Ethnic Group | Genotype 2756A-G | Cases N | Cases % | Controls N | Controls % | Odds ratio* | 95% C.I. |
|---|---|---|---|---|---|---|---|
| Overall | Asp/Asp | 64 | 67 | 104 | 64 | 1.0 | |
| | Asp/Gly | 30 | 32 | 49 | 30 | 0.99 | 0.56–1.72 |
| | Gly/Gly | 1 | 1 | 7 | 4 | 0.23 | 0.05–1.92 |
| White only | Asp/Asp | 21 | 66 | 38 | 66 | 2.0 | |
| | Asp/Gly | 10 | 31 | 16 | 28 | 1.1 | 0.44–2.9 |
| | Gly/Gly | 1 | 3 | 3 | 5 | 0.60 | 0.11–5.6 |
| Hispanic only | Asp/Asp | 43 | 68 | 66 | 63 | 1.0 | |
| | Asp/Gly | 20 | 32 | 33 | 31 | 0.9 | 0.45–1.8 |
| | Gly/Gly | 0 | 0 | 4 | 4 | 0 | |

*Odds ration calculated for genotypes Asp/Asp vs Gly/Gly

TABLE 4

Frequency of MS genotype and relative risk (RR) of colorectal cancer by MS genotype

| MS Genotype | Cases n | Cases % | Controls n | Controls % | RR | 95% CI |
|---|---|---|---|---|---|---|
| Asp/Asp | 145 | (68) | 234 | (68) | 1.0 | |
| Asp/Gly | 61 | (29) | 95 | (28) | 1.02 | 0.69–1.50 |
| Gly/Gly | 6 | (3) | 16 | (5) | 0.62 | 0.24–1.64 |
| Total | 212 | | 345 | | | |

TABLE 5

Mean of homocysteine and folate (geometric) by case control status and MS Genotype in a colon cancer study

| MS genotype | Cases n | Cases mean | Controls n | Controls mean | Cases & Controls n | Cases & Controls mean |
|---|---|---|---|---|---|---|
| | | Folate (Bio-Kit) ng/ml | | | | |
| Asp/Asp | 115 | 3.8 | 201 | 3.9* | 316 | 3.9** |
| Asp/Gly | 49 | 4.1* | 80 | 3.8* | 129 | 3.9** |
| Gly/Gly | 6 | 2.1 | 12 | 2.3 | 18 | 2.2 |
| | | Homocysteine ($\mu M$) | | | | |
| Asp/Asp | 66 | 12.5 | 160 | 12.1 | 226 | 12.3 |
| Asp/Gly | 30 | 10.8 | 50 | 11.6 | 80 | 11.2 |
| Gly/Gly | 4 | 13.4 | 9 | 11.7 | 13 | 12.5 |

* = $p < 0.05$
** = $p < 0.01$

TABLE 6

Age Adjusted Relative Risk of Colon Cancer According to MS Polymorphism and Alcohol Intake Status Among US Physicians

| Alcohol intake | Genotype 2756A–>G Asp919Gly | Cases N | Controls N | Odds ratio | 95% C.I. |
|---|---|---|---|---|---|
| Low–Medium 0–0.8 drinks/day | Asp/Asp | 1013 | 2e + 09 | 1.0 | |
| | Asp/Gly | 7113 | | 0.87 | 0.54–1.4 |
| | Gly/Gly | 9 | | 0.11 | 0.01–0.82 |
| | N | | | | |
| High 1–2+ drinks/day | Asp/Asp | 3721 | 7e + 06 | 0.74 | 0.46–1.19 |
| | Asp/Gly | 563 | | 1.15 | 0.60–2.18 |
| | Gly/Gly | | | 3.83 | 0.72–20.47 |
| | N | | | | |

What is claimed is:

1. A substantially pure nucleic acid, wherein said nucleic acid has the sequence of SEQ ID NO: 1, or degenerate variants thereof, and wherein said nucleic acid encodes the amino acid sequence of SEQ ID NO: 2.

2. A method for detecting sequence variants for methionine synthase in a human patient, said method comprising analyzing the nucleic acid of a human to determine whether said human contains a homozygous D919G mutation in a methionine synthase nucleic acid, wherein the presence of said mutation is an indication that said human has a decreased risk for a neural tube defect, a decreased risk for colon cancer, an increased risk of developing hyperhomocysteinemia, or an increased risk of developing cardiovascular disease.

3. The method of claim 2, wherein said method further comprises the step of sequencing a fragment of said nucleic acid encoding human methionine synthase.

4. The method of claim 2, wherein said method further comprises the step of using nucleic acid primers specific for the methionine synthase gene and wherein said primers are used for DNA amplification by the polymerase chain reaction.

5. A substantially pure nucleic acid comprising at least 40 nucleotides that hybridizes at high stringency to a sequence found within the nucleic acid of SEQ ID NO:1, wherein said nucleic acid comprises a mutation or polymorphism selected from the group consisting of D919G, H920D, and ΔIle881.

6. A kit for the analysis of a human methionine synthase nucleic acid, said kit comprising a nucleic acid probe useful for detecting in the nucleic acids of a human a mutation in said methionine synthase nucleic acid, wherein said nucleic acid probe detects a mutation or polymorphism corresponding to D919G, H920D, and ΔIle881 of said human methionine synthase nucleic acid.

* * * * *

SEQUENCE LISTING

<160> NUMBER OF SEQ ID NOS: 76

<210> SEQ ID NO 1
<211> LENGTH: 3919

<212> TYPE: DNA
<213> ORGANISM: Homo sapiens
<220> FEATURE:
<221> NAME/KEY: Other
<222> LOCATION: (1)...(3919)
<223> OTHER INFORMATION: Entire cloned cDNA encoding wild type
      methionine synthase.

<400> SEQUENCE: 1

| | | | | | |
|---|---|---|---|---|---|
| ggtcacctgt | ggagagcacg | tcttctctgc | cgcgccctct | gcgcaaggag | gagactcgac | 60 |
| aacatgtcac | ccgcgctcca | agacctgtcg | caacccgaag | gtctgaagaa | aaccctgcgg | 120 |
| gatgagatca | atgccattct | gcagaagagg | attatggtgc | tggatggagg | gatggggacc | 180 |
| atgatccagc | gggagaagct | aaacgaagaa | cacttccgag | gtcaggaatt | taaagatcat | 240 |
| gccaggccgc | tgaaaggcaa | caatgacatt | ttaagtataa | ctcagcctga | tgtcatttac | 300 |
| caaatccata | ggaatactt | gctggctggg | gcagatatca | ttgaaacaaa | tacttttagc | 360 |
| agcactagta | ttgcccaagc | tgactatggc | cttgaacact | tggcctaccg | gatgaacatg | 420 |
| tgctctgcag | gagtggccag | aaaagctgcc | gaggaggtaa | ctctccagac | aggaattaag | 480 |
| aggtttgtgg | cagggctct | gggtccgact | aataagacac | tctctgtgtc | cccatctgtg | 540 |
| gaaaggccgg | attataggaa | catcacattt | gatgagcttg | ttgaagcata | ccaagagcag | 600 |
| gccaaaggac | ttctggatgg | cggggttgat | atcttactca | ttgaaactat | ttttgatact | 660 |
| gccaatgcca | aggcagcctt | gtttgcactc | caaaatcttt | ttgaggagaa | atatgctccc | 720 |
| cggcctatct | ttatttcagg | gacgatcgtt | gataaaagtg | ggcggactct | ttccggacag | 780 |
| acaggagagg | gatttgtcat | cagcgtgtct | catggagaac | cactctgcat | tggattaaat | 840 |
| tgtgctttgg | gtgcagctga | gatgagacct | tttattgaaa | taattggaaa | atgtacaaca | 900 |
| gcctatgtcc | tctgttatcc | caatgcaggt | cttcccaaca | cctttggtga | ctatgatgaa | 960 |
| acgccttcta | tgatggccaa | gcacctaaag | gattttgcta | tggatggctt | ggtcaatata | 1020 |
| gttggaggat | gctgtgggtc | aacaccagat | catatcaggg | aaattgctga | agctgtgaaa | 1080 |
| aattgtaagc | ctagagttcc | acctgccact | gcttttgaag | gacatatgtt | actgtctggt | 1140 |
| ctagagccct | tcaggattgg | accgtacacc | aactttgtta | acattggaga | gcgctgtaat | 1200 |
| gttgcaggat | caaggaagtt | tgctaaactc | atcatggcag | gaaactatga | agaagccttg | 1260 |
| tgtgttgcca | agtgcaggt | ggaaatggga | gcccaggtgt | tggatgtcaa | catggatgat | 1320 |
| ggcatgctag | atggtccaag | tgcaatgacc | agatttgca | acttaattgc | ttccgagcca | 1380 |
| gacatcgcaa | aggtacctt | gtgcatcgac | tcctccaatt | ttgctgtgat | tgaagctggg | 1440 |
| ttaaagtgct | gccaagggaa | gtgcattgtc | aatagcatta | gtcgaagga | aggagaggac | 1500 |
| gacttcttgg | agaaggccag | gaagattaaa | agtatggag | ctgctatggt | ggtcatggct | 1560 |
| tttgatgaag | aaggacaggc | aacagaaaca | gacacaaaaa | tcagagtgtg | cacccgggcc | 1620 |
| taccatctgc | ttgtgaaaaa | actgggcttt | aatccaaatg | acattatttt | tgaccctaat | 1680 |
| atcctaacca | ttgggactgg | aatggaggaa | cacaacttgt | atgccattaa | ttttatccat | 1740 |
| gcaacaaaag | tcattaaaga | aacattacct | ggagccagaa | taagtggagg | tctttccaac | 1800 |
| ttgtccttct | ccttccgagg | aatggaagcc | attcgagaag | caatgcatgg | ggttttcctt | 1860 |
| taccatgcaa | tcaagtctgg | catggacatg | gagatagtga | atgctggaaa | cctccctgtg | 1920 |
| tatgatgata | tccataagga | acttctgcag | ctctgtgaag | atctcatctg | gaataaagac | 1980 |
| cctgaggcca | ctgagaagct | cttacgttat | gcccagactc | aaggcacagg | agggaagaaa | 2040 |
| gtcattcaga | ctgatgagtg | gagaaatggc | cctgtcgaag | aacgccttga | gtatgccctt | 2100 |

-continued

```
gtgaagggca ttgaaaaaca tattattgag gatactgagg aagccaggtt aaaccaaaaa    2160
aaatatcccc gacctctcaa tataattgaa ggacccctga tgaatggaat gaaaattgtt    2220
ggtgatcttt ttggagctgg aaaaatgttt ctacctcagg ttataaagtc agcccgggtt    2280
atgaagaagg ctgttggcca ccttatccct ttcatggaaa aagaaagaga agaaaccaga    2340
gtgcttaacg gcacagtaga agaagaggac ccttaccagg gcaccatcgt gctggccact    2400
gttaaaggcg acgtgcacga cataggcaag aacatagttg gagtagtcct tggctgcaat    2460
aatttccgag ttattgattt aggagtcatg actccatgtg ataagatact gaaagctgct    2520
cttgaccaca aagcagatat aattggcctg tcaggactca tcactccttc cctggatgaa    2580 atgattttg ttgccaagga aatggagaga ttagctataa ggattccatt gttgattgga    2640
ggagcaacca cttcaaaaac ccacacagca gttaaaatag ctccgagata cagtgcacct    2700
gtaatccatg tcctggacgc gtccaagagt gtggtggtgt gttcccagct gttagatgaa    2760
aatctaaagg atgaatactt tgaggaaatc atggaagaat atgaagatat tagacaggac    2820
cattatgagt ctctcaagga gaggagatac ttacccttaa gtcaagccag aaaaagtggt    2880
ttccaaatgg attggctgtc tgaacctcac ccagtgaagc ccacgtttat tgggacccag    2940
gtctttgaag actatgacct gcagaagctg gtggactaca ttgactggaa gcctttcttt    3000
gatgtctggc agctccgggg caagtacccg aatcgaggct cccccaagat atttaacgac    3060
aaaacagtag gtggagaggc caggaaggtc tacgatgatg cccacaatat gctgaacaca    3120
ctgattagtc aaaagaaact ccgggcccgg ggtgtggttg ggttctggcc agcacagagt    3180
atccaagacg acattcacct gtacgcagag gctgctgtgc cccaggctgc agagcccata    3240
gccactttct atgggttaag gcaacaggct gagaaggact ctgccagcac ggagccatac    3300
tactgcctct cagacttcat cgctcccttg cattctggca tccgtgacta cctgggcctg    3360
tttgccgttg cctgctttgg ggtagaagag ctgagcaagg cctatgagga tgatggtgac    3420
gactacagca gcatcatggt caaggcgctg ggggaccggc tggcagaggc ctttgcagaa    3480
gagctccatg aaagagttcg ccgagaactg tgggcctact gtggcagtga gcagctggac    3540
gtcgcagacc tgcgaaggtt gcggtacaag ggcatccgcc cggctcctgg ctaccccagc    3600
cagcccgacc acaccgagaa gctcaccatg tggagactcg cagacatcga gcagtctaca    3660
ggcattaggt taacagaatc attagcaatg gcacctgctt cagcagtctc aggcctctac    3720
ttctccaatt tgaagtccaa atattttgct gtggggaaga tttccaagga tcaggttgag    3780
gattatgcat tgaggaagaa catatctgtg gctgaggttg agaaatggct tggacccatt    3840
ttgggatatg atacagacta acttttttttt tttttttgc cttttttatc ttgatgatcc    3900
tcaaggaaat acaacctag                                                  3919
```

<210> SEQ ID NO 2
<211> LENGTH: 1265
<212> TYPE: PRT
<213> ORGANISM: Homo sapiens
<220> FEATURE:
<221> NAME/KEY: VARIANT
<222> LOCATION: (1)...(1265)
<223> OTHER INFORMATION: Wild type methionine synthase polypeptide.

<400> SEQUENCE: 2

Met Ser Pro Ala Leu Gln Asp Leu Ser Gln Pro Glu Gly Leu Lys Lys
 1               5                  10                  15

Thr Leu Arg Asp Glu Ile Asn Ala Ile Leu Gln Lys Arg Ile Met Val

-continued

```
                    20                  25                  30
Leu Asp Gly Gly Met Gly Thr Met Ile Gln Arg Glu Lys Leu Asn Glu
                35                  40                  45
Glu His Phe Arg Gly Gln Glu Phe Lys Asp His Ala Arg Pro Leu Lys
         50                  55                  60
Gly Asn Asn Asp Ile Leu Ser Ile Thr Gln Pro Asp Val Ile Tyr Gln
 65                  70                  75                  80
Ile His Lys Glu Tyr Leu Leu Ala Gly Ala Asp Ile Ile Glu Thr Asn
                 85                  90                  95
Thr Phe Ser Ser Thr Ser Ile Ala Gln Ala Asp Tyr Gly Leu Glu His
            100                 105                 110
Leu Ala Tyr Arg Met Asn Met Cys Ser Ala Gly Val Ala Arg Lys Ala
            115                 120                 125
Ala Glu Glu Val Thr Leu Gln Thr Gly Ile Lys Arg Phe Val Ala Gly
            130                 135                 140
Ala Leu Gly Pro Thr Asn Lys Thr Leu Ser Val Ser Pro Ser Val Glu
 145                 150                 155                 160
Arg Pro Asp Tyr Arg Asn Ile Thr Phe Asp Glu Leu Val Glu Ala Tyr
                165                 170                 175
Gln Glu Gln Ala Lys Gly Leu Leu Asp Gly Val Asp Ile Leu Leu
            180                 185                 190
Ile Glu Thr Ile Phe Asp Thr Ala Asn Ala Lys Ala Ala Leu Phe Ala
            195                 200                 205
Leu Gln Asn Leu Phe Glu Glu Lys Tyr Ala Pro Arg Pro Ile Phe Ile
            210                 215                 220
Ser Gly Thr Ile Val Asp Lys Ser Gly Arg Thr Leu Ser Gly Gln Thr
 225                 230                 235                 240
Gly Glu Gly Phe Val Ile Ser Val Ser His Gly Glu Pro Leu Cys Ile
                245                 250                 255
Gly Leu Asn Cys Ala Leu Gly Ala Ala Glu Met Arg Pro Phe Ile Glu
            260                 265                 270
Ile Ile Gly Lys Cys Thr Thr Ala Tyr Val Leu Cys Tyr Pro Asn Ala
            275                 280                 285
Gly Leu Pro Asn Thr Phe Gly Asp Tyr Asp Glu Thr Pro Ser Met Met
            290                 295                 300
Ala Lys His Leu Lys Asp Phe Ala Met Asp Gly Leu Val Asn Ile Val
 305                 310                 315                 320
Gly Gly Cys Cys Gly Ser Thr Pro Asp His Ile Arg Glu Ile Ala Glu
                325                 330                 335
Ala Val Lys Asn Cys Lys Pro Arg Val Pro Ala Thr Ala Phe Glu
            340                 345                 350
Gly His Met Leu Leu Ser Gly Leu Glu Pro Phe Arg Ile Gly Pro Tyr
            355                 360                 365
Thr Asn Phe Val Asn Ile Gly Glu Arg Cys Asn Val Ala Gly Ser Arg
            370                 375                 380
Lys Phe Ala Lys Leu Ile Met Ala Gly Asn Tyr Glu Glu Ala Leu Cys
 385                 390                 395                 400
Val Ala Lys Val Gln Val Glu Met Gly Ala Gln Val Leu Asp Val Asn
            405                 410                 415
Met Asp Asp Gly Met Leu Asp Gly Pro Ser Ala Met Thr Arg Phe Cys
            420                 425                 430
Asn Leu Ile Ala Ser Glu Pro Asp Ile Ala Lys Val Pro Leu Cys Ile
            435                 440                 445
```

```
Asp Ser Ser Asn Phe Ala Val Ile Glu Ala Gly Leu Lys Cys Cys Gln
    450                 455                 460

Gly Lys Cys Ile Val Asn Ser Ile Ser Leu Lys Glu Gly Asp Asp
465                 470                 475                 480

Phe Leu Glu Lys Ala Arg Lys Ile Lys Lys Tyr Gly Ala Ala Met Val
                485                 490                 495

Val Met Ala Phe Asp Glu Gly Gln Ala Thr Glu Thr Asp Thr Lys
            500                 505                 510

Ile Arg Val Cys Thr Arg Ala Tyr His Leu Leu Val Lys Lys Leu Gly
            515                 520                 525

Phe Asn Pro Asn Asp Ile Ile Phe Asp Pro Asn Ile Leu Thr Ile Gly
    530                 535                 540

Thr Gly Met Glu Glu His Asn Leu Tyr Ala Ile Asn Phe Ile His Ala
545                 550                 555                 560

Thr Lys Val Ile Lys Glu Thr Leu Pro Gly Ala Arg Ile Ser Gly Gly
                565                 570                 575

Leu Ser Asn Leu Ser Phe Ser Phe Arg Gly Met Glu Ala Ile Arg Glu
            580                 585                 590

Ala Met His Gly Val Phe Leu Tyr His Ala Ile Lys Ser Gly Met Asp
                595                 600                 605

Met Glu Ile Val Asn Ala Gly Asn Leu Pro Val Tyr Asp Asp Ile His
    610                 615                 620

Lys Glu Leu Leu Gln Leu Cys Glu Asp Leu Ile Trp Asn Lys Asp Pro
625                 630                 635                 640

Glu Ala Thr Glu Lys Leu Leu Arg Tyr Ala Gln Thr Gln Gly Thr Gly
                645                 650                 655

Gly Lys Lys Val Ile Gln Thr Asp Glu Trp Arg Asn Gly Pro Val Glu
            660                 665                 670

Glu Arg Leu Glu Tyr Ala Leu Val Lys Gly Ile Glu Lys His Ile Ile
        675                 680                 685

Glu Asp Thr Glu Ala Arg Leu Asn Gln Lys Lys Tyr Pro Arg Pro
    690                 695                 700

Leu Asn Ile Ile Glu Gly Pro Leu Met Asn Gly Met Lys Ile Val Gly
705                 710                 715                 720

Asp Leu Phe Gly Ala Gly Lys Met Phe Leu Pro Gln Val Ile Lys Ser
                725                 730                 735

Ala Arg Val Met Lys Lys Ala Val Gly His Leu Ile Pro Phe Met Glu
            740                 745                 750

Lys Glu Arg Glu Glu Thr Arg Val Leu Asn Gly Thr Val Glu Glu Glu
        755                 760                 765

Asp Pro Tyr Gln Gly Thr Ile Val Leu Ala Thr Val Lys Gly Asp Val
    770                 775                 780

His Asp Ile Gly Lys Asn Ile Val Gly Val Val Leu Gly Cys Asn Asn
785                 790                 795                 800

Phe Arg Val Ile Asp Leu Gly Val Met Thr Pro Cys Asp Lys Ile Leu
            805                 810                 815

Lys Ala Ala Leu Asp His Lys Ala Asp Ile Ile Gly Leu Ser Gly Leu
        820                 825                 830

Ile Thr Pro Ser Leu Asp Glu Met Ile Phe Val Ala Lys Glu Met Glu
    835                 840                 845

Arg Leu Ala Ile Arg Ile Pro Leu Leu Ile Gly Gly Ala Thr Thr Ser
850                 855                 860
```

-continued

```
Lys Thr His Thr Ala Val Lys Ile Ala Pro Arg Tyr Ser Ala Pro Val
865                 870                 875                 880

Ile His Val Leu Asp Ala Ser Lys Ser Val Val Cys Ser Gln Leu
            885                 890                 895

Leu Asp Glu Asn Leu Lys Asp Glu Tyr Phe Glu Ile Met Glu Glu
            900                 905                 910

Tyr Glu Asp Ile Arg Gln Asp His Tyr Glu Ser Leu Lys Glu Arg Arg
                915                 920                 925

Tyr Leu Pro Leu Ser Gln Ala Arg Lys Ser Gly Phe Gln Met Asp Trp
930                 935                 940

Leu Ser Glu Pro His Pro Val Lys Pro Thr Phe Ile Gly Thr Gln Val
945                 950                 955                 960

Phe Glu Asp Tyr Asp Leu Gln Lys Leu Val Asp Tyr Ile Asp Trp Lys
                965                 970                 975

Pro Phe Phe Asp Val Trp Gln Leu Arg Gly Lys Tyr Pro Asn Arg Gly
            980                 985                 990

Phe Pro Lys Ile Phe Asn Asp Lys Thr Val Gly Gly Glu Ala Arg Lys
        995                 1000                1005

Val Tyr Asp Asp Ala His Asn Met Leu Asn Thr Leu Ile Ser Gln Lys
        1010                1015                1020

Lys Leu Arg Ala Arg Gly Val Val Gly Phe Trp Pro Ala Gln Ser Ile
1025                1030                1035                104

Gln Asp Asp Ile His Leu Tyr Ala Glu Ala Ala Val Pro Gln Ala Ala
                1045                1050                1055

Glu Pro Ile Ala Thr Phe Tyr Gly Leu Arg Gln Gln Ala Glu Lys Asp
            1060                1065                1070

Ser Ala Ser Thr Glu Pro Tyr Tyr Cys Leu Ser Asp Phe Ile Ala Pro
            1075                1080                1085

Leu His Ser Gly Ile Arg Asp Tyr Leu Gly Leu Phe Ala Val Ala Cys
        1090                1095                1100

Phe Gly Val Glu Glu Leu Ser Lys Ala Tyr Glu Asp Asp Gly Asp Asp
1105                1110                1115                112

Tyr Ser Ser Ile Met Val Lys Ala Leu Gly Asp Arg Leu Ala Glu Ala
            1125                1130                1135

Phe Ala Glu Glu Leu His Glu Arg Val Arg Arg Glu Leu Trp Ala Tyr
            1140                1145                1150

Cys Gly Ser Glu Gln Leu Asp Val Ala Asp Leu Arg Arg Leu Arg Tyr
        1155                1160                1165

Lys Gly Ile Arg Pro Ala Pro Gly Tyr Pro Ser Gln Pro Asp His Thr
1170                1175                1180

Glu Lys Leu Thr Met Trp Arg Leu Ala Asp Ile Glu Gln Ser Thr Gly
1185                1190                1195                120

Ile Arg Leu Thr Glu Ser Leu Ala Met Ala Pro Ala Ser Ala Val Ser
            1205                1210                1215

Gly Leu Tyr Phe Ser Asn Leu Ser Lys Tyr Phe Ala Val Gly Lys
            1220                1225                1230

Ile Ser Lys Asp Gln Val Glu Asp Tyr Ala Leu Arg Lys Asn Ile Ser
        1235                1240                1245

Val Ala Glu Val Glu Lys Trp Leu Gly Pro Ile Leu Gly Tyr Asp Thr
    1250                1255                1260

Asp
1265
```

```
<210> SEQ ID NO 3
<211> LENGTH: 9
<212> TYPE: PRT
<213> ORGANISM: Escherichia coli

<400> SEQUENCE: 3

Asp Gly Gly Met Gly Thr Met Ile Gln
 1               5

<210> SEQ ID NO 4
<211> LENGTH: 9
<212> TYPE: PRT
<213> ORGANISM: Cyanobacterium synechocystis

<400> SEQUENCE: 4

Asp Gly Ala Met Gly Thr Asn Leu Gln
 1               5

<210> SEQ ID NO 5
<211> LENGTH: 9
<212> TYPE: PRT
<213> ORGANISM: Mycobacterium leprae

<400> SEQUENCE: 5

Asp Gly Ala Met Gly Thr Gln Leu Gln
 1               5

<210> SEQ ID NO 6
<211> LENGTH: 9
<212> TYPE: PRT
<213> ORGANISM: Hemophilus influenzae

<400> SEQUENCE: 6

Asp Gly Ala Met Gly Thr Met Ile Gln
 1               5

<210> SEQ ID NO 7
<211> LENGTH: 9
<212> TYPE: PRT
<213> ORGANISM: Caenorrhabditis elegans

<400> SEQUENCE: 7

Asp Gly Ala Met Gly Thr Met Ile Gln
 1               5

<210> SEQ ID NO 8
<211> LENGTH: 9
<212> TYPE: PRT
<213> ORGANISM: Homo sapiens

<400> SEQUENCE: 8

Asp Gly Gly Met Gly Thr Met Ile Gln
 1               5

<210> SEQ ID NO 9
<211> LENGTH: 13
<212> TYPE: PRT
<213> ORGANISM: Escherichia coli

<400> SEQUENCE: 9

Ala Thr Val Lys Gly Asp Val His Asp Ile Gly Lys Asn
 1               5                  10

<210> SEQ ID NO 10
<211> LENGTH: 13
```

<212> TYPE: PRT
<213> ORGANISM: Cyanobacterium synechocystis

<400> SEQUENCE: 10

Ala Thr Val Lys Gly Asp Val His Asp Ile Gly Lys Asn
1               5                   10

<210> SEQ ID NO 11
<211> LENGTH: 13
<212> TYPE: PRT
<213> ORGANISM: Mycobacterium leprae

<400> SEQUENCE: 11

Ala Thr Val Lys Gly Asp Val His Asp Ile Gly Lys Asn
1               5                   10

<210> SEQ ID NO 12
<211> LENGTH: 13
<212> TYPE: PRT
<213> ORGANISM: Hemophilus influenzae

<400> SEQUENCE: 12

Ala Thr Val Lys Gly Asp Val His Asp Ile Gly Lys Asn
1               5                   10

<210> SEQ ID NO 13
<211> LENGTH: 13
<212> TYPE: PRT
<213> ORGANISM: Caenorrhabditis elegans

<400> SEQUENCE: 13

Ala Thr Val Lys Gly Asp Val His Asp Ile Gly Lys Asn
1               5                   10

<210> SEQ ID NO 14
<211> LENGTH: 13
<212> TYPE: PRT
<213> ORGANISM: Homo sapiens

<400> SEQUENCE: 14

Ala Thr Val Lys Gly Asp Val His Asp Ile Gly Lys Asn
1               5                   10

<210> SEQ ID NO 15
<211> LENGTH: 10
<212> TYPE: PRT
<213> ORGANISM: Escherichia coli

<400> SEQUENCE: 15

Leu Ala Glu Ala Phe Ala Glu Tyr Leu His
1               5                   10

<210> SEQ ID NO 16
<211> LENGTH: 10
<212> TYPE: PRT
<213> ORGANISM: Cyanobacterium synechocystis

<400> SEQUENCE: 16

Met Ala Glu Ala Leu Ala Glu Trp Thr His
1               5                   10

<210> SEQ ID NO 17
<211> LENGTH: 10
<212> TYPE: PRT
<213> ORGANISM: Mycobacterium leprae

```
<400> SEQUENCE: 17

Leu Thr Glu Ala Leu Ala Glu Tyr Trp His
  1               5                  10

<210> SEQ ID NO 18
<211> LENGTH: 10
<212> TYPE: PRT
<213> ORGANISM: Hemophilus influenzae

<400> SEQUENCE: 18

Leu Ala Glu Ala Met Ala Glu Tyr Leu His
  1               5                  10

<210> SEQ ID NO 19
<211> LENGTH: 10
<212> TYPE: PRT
<213> ORGANISM: Caenorrhabditis elegans

<400> SEQUENCE: 19

Leu Ala Glu Ala Tyr Ala Glu Tyr Leu His
  1               5                  10

<210> SEQ ID NO 20
<211> LENGTH: 10
<212> TYPE: PRT
<213> ORGANISM: Homo sapiens

<400> SEQUENCE: 20

Leu Ala Glu Ala Phe Ala Glu Glu Leu His
  1               5                  10

<210> SEQ ID NO 21
<211> LENGTH: 11
<212> TYPE: PRT
<213> ORGANISM: Escherichia coli

<400> SEQUENCE: 21

Gly Gly Cys Cys Gly Thr Thr Pro Gln His Ile
  1               5                  10

<210> SEQ ID NO 22
<211> LENGTH: 11
<212> TYPE: PRT
<213> ORGANISM: Cyanobacterium synechocystis

<400> SEQUENCE: 22

Gly Gly Cys Cys Gly Thr Arg Pro Asp His Ile
  1               5                  10

<210> SEQ ID NO 23
<211> LENGTH: 11
<212> TYPE: PRT
<213> ORGANISM: Mycobacterium leprae

<400> SEQUENCE: 23

Gly Gly Cys Cys Gly Thr Thr Pro Asp His Ile
  1               5                  10

<210> SEQ ID NO 24
<211> LENGTH: 11
<212> TYPE: PRT
<213> ORGANISM: Caenorrhabditis elegans

<400> SEQUENCE: 24
```

Gly Gly Cys Cys Gly Thr Thr Pro Asp His Ile
1               5                   10

<210> SEQ ID NO 25
<211> LENGTH: 11
<212> TYPE: PRT
<213> ORGANISM: Homo sapiens

<400> SEQUENCE: 25

Gly Gly Cys Cys Gly Ser Thr Pro Asp His Ile
1               5                   10

<210> SEQ ID NO 26
<211> LENGTH: 26
<212> TYPE: DNA
<213> ORGANISM: Homo sapiens
<220> FEATURE:
<221> NAME/KEY: variation
<222> LOCATION: (1)...(26)
<223> OTHER INFORMATION: n is a, t, g, or c; h is a, c, or t; d is
      a, g, or t; and r is a or g;

<400> SEQUENCE: 26
gayggngcna tgggnacnat gathca                                         26

<210> SEQ ID NO 27
<211> LENGTH: 29
<212> TYPE: DNA
<213> ORGANISM: Homo sapiens
<220> FEATURE:
<221> NAME/KEY: variation
<222> LOCATION: (1)...(29)
<223> OTHER INFORMATION: n is a, t, g, or c; h is a, c, or t; d is
      a, g, or t; and r is a or g;

<400> SEQUENCE: 27
gcnacngtna arggngaygt ncaygayat                                      29

<210> SEQ ID NO 28
<211> LENGTH: 30
<212> TYPE: DNA
<213> ORGANISM: Homo sapiens
<220> FEATURE:
<221> NAME/KEY: variation
<222> LOCATION: (1)...(30)
<223> OTHER INFORMATION: n is a, t, g, or c; h is a, c, or t; d is
      a, g, or t; and r is a or g;

<400> SEQUENCE: 28
rttyttnccd atrtcrtgna crtcnccytt                                     30

<210> SEQ ID NO 29
<211> LENGTH: 27
<212> TYPE: DNA
<213> ORGANISM: Homo sapiens
<220> FEATURE:
<221> NAME/KEY: variation
<222> LOCATION: (1)...(27)
<223> OTHER INFORMATION: n is a, t, g, or c; h is a, c, or t; d is
      a, g, or t; and r is a or g;

<400> SEQUENCE: 29
rtgnagrtay tcngcraang cytcngc                                        27

<210> SEQ ID NO 30
<211> LENGTH: 32
<212> TYPE: DNA

```
<213> ORGANISM: Homo sapiens
<220> FEATURE:
<221> NAME/KEY: variation
<222> LOCATION: (1)...(32)
<223> OTHER INFORMATION: n is a, t, g, or c; h is a, c, or t; d is
      a, g, or t; and r is a or g;

<400> SEQUENCE: 30
atrtgrtcng gngtngtncc rcarcanccn cc                              32

<210> SEQ ID NO 31
<211> LENGTH: 32
<212> TYPE: DNA
<213> ORGANISM: Homo sapiens
<220> FEATURE:
<221> NAME/KEY: variation
<222> LOCATION: (1)...(32)
<223> OTHER INFORMATION: n is a, t, g, or c; h is a, c, or t; d is
      a, g, or t; and r is a or g;

<400> SEQUENCE: 31
ggnggntgyt gyggnacnac nccngaycay at                              32

<210> SEQ ID NO 32
<211> LENGTH: 24
<212> TYPE: DNA
<213> ORGANISM: Mus musculus

<400> SEQUENCE: 32
gtctgtgtca tagcccagaa tggg                                       24

<210> SEQ ID NO 33
<211> LENGTH: 24
<212> TYPE: DNA
<213> ORGANISM: Mus musculus

<400> SEQUENCE: 33
tcagtctgtg tcatagccca gaat                                       24

<210> SEQ ID NO 34
<211> LENGTH: 24
<212> TYPE: DNA
<213> ORGANISM: Homo sapiens

<400> SEQUENCE: 34
gaactagaag acagaaattc tcta                                       24

<210> SEQ ID NO 35
<211> LENGTH: 26
<212> TYPE: DNA
<213> ORGANISM: Homo sapiens

<400> SEQUENCE: 35
ttccgaggtc aggaatttaa agatca                                     26

<210> SEQ ID NO 36
<211> LENGTH: 24
<212> TYPE: DNA
<213> ORGANISM: Homo sapiens

<400> SEQUENCE: 36
gtgttcttcg tttagcttct cccg                                       24

<210> SEQ ID NO 37
<211> LENGTH: 24
```

-continued

```
<212> TYPE: DNA
<213> ORGANISM: Homo sapiens

<400> SEQUENCE: 37
ccccagccag caagtattcc ttat                                      24

<210> SEQ ID NO 38
<211> LENGTH: 24
<212> TYPE: DNA
<213> ORGANISM: Homo sapiens

<400> SEQUENCE: 38
ctaggttgta tttccttgag gatc                                      24

<210> SEQ ID NO 39
<211> LENGTH: 25
<212> TYPE: DNA
<213> ORGANISM: Homo sapiens

<400> SEQUENCE: 39
ggagctggaa aaatgtttct acctc                                     25

<210> SEQ ID NO 40
<211> LENGTH: 24
<212> TYPE: DNA
<213> ORGANISM: Homo sapiens

<400> SEQUENCE: 40
acaggaggga agaaagtcat tcag                                      24

<210> SEQ ID NO 41
<211> LENGTH: 25
<212> TYPE: DNA
<213> ORGANISM: Homo sapiens

<400> SEQUENCE: 41
ccttcaatta tattgagagg tcggg                                     25

<210> SEQ ID NO 42
<211> LENGTH: 24
<212> TYPE: DNA
<213> ORGANISM: Homo sapiens

<400> SEQUENCE: 42
caacccgaag gtctgaagaa aacc                                      24

<210> SEQ ID NO 43
<211> LENGTH: 21
<212> TYPE: DNA
<213> ORGANISM: Homo sapiens

<400> SEQUENCE: 43
cccgcgctcc aagacctgtc g                                         21

<210> SEQ ID NO 44
<211> LENGTH: 21
<212> TYPE: DNA
<213> ORGANISM: Homo sapiens

<400> SEQUENCE: 44
cgacaggtct tggagcgcgg g                                         21

<210> SEQ ID NO 45
```

-continued

```
<211> LENGTH: 28
<212> TYPE: DNA
<213> ORGANISM: Homo sapiens

<400> SEQUENCE: 45
ggagtcatga ctcctaaatc aataactc                                          28

<210> SEQ ID NO 46
<211> LENGTH: 23
<212> TYPE: DNA
<213> ORGANISM: Homo sapiens

<400> SEQUENCE: 46
gacgactaca gcagcatcat ggt                                               23

<210> SEQ ID NO 47
<211> LENGTH: 22
<212> TYPE: DNA
<213> ORGANISM: Homo sapiens

<400> SEQUENCE: 47
aaaaatcatt tcatccaggg aa                                                22

<210> SEQ ID NO 48
<211> LENGTH: 26
<212> TYPE: DNA
<213> ORGANISM: Homo sapiens

<400> SEQUENCE: 48
ataggcaaga acatagttgg agtagt                                            26

<210> SEQ ID NO 49
<211> LENGTH: 25
<212> TYPE: DNA
<213> ORGANISM: Homo sapiens

<400> SEQUENCE: 49
tttcatctaa cagctgggaa cacac                                             25

<210> SEQ ID NO 50
<211> LENGTH: 24
<212> TYPE: DNA
<213> ORGANISM: Homo sapiens

<400> SEQUENCE: 50
tgcctctcag acttcatcgc tccc                                              24

<210> SEQ ID NO 51
<211> LENGTH: 21
<212> TYPE: DNA
<213> ORGANISM: Homo sapiens

<400> SEQUENCE: 51
tgcagcctgg ggcacagcag c                                                 21

<210> SEQ ID NO 52
<211> LENGTH: 24
<212> TYPE: DNA
<213> ORGANISM: Homo sapiens

<400> SEQUENCE: 52
atggattggc tgtctgaacc tcac                                              24
```

-continued

<210> SEQ ID NO 53
<211> LENGTH: 26
<212> TYPE: DNA
<213> ORGANISM: Homo sapiens

<400> SEQUENCE: 53
catggaagaa tatgaagata ttagac                                    26

<210> SEQ ID NO 54
<211> LENGTH: 24
<212> TYPE: DNA
<213> ORGANISM: Homo sapiens

<400> SEQUENCE: 54
accatcatcc tcataggcct tgct                                      24

<210> SEQ ID NO 55
<211> LENGTH: 23
<212> TYPE: DNA
<213> ORGANISM: Homo sapiens

<400> SEQUENCE: 55
cagacctgcg aaggttgcgg tac                                       23

<210> SEQ ID NO 56
<211> LENGTH: 24
<212> TYPE: DNA
<213> ORGANISM: Homo sapiens

<400> SEQUENCE: 56
gaagtggttg ctcctccaat caac                                      24

<210> SEQ ID NO 57
<211> LENGTH: 26
<212> TYPE: DNA
<213> ORGANISM: Homo sapiens

<400> SEQUENCE: 57
gagcagcttt cagtatctta tcacat                                    26

<210> SEQ ID NO 58
<211> LENGTH: 25
<212> TYPE: DNA
<213> ORGANISM: Homo sapiens

<400> SEQUENCE: 58
acaagttgtg ttcctccatt ccagt                                     25

<210> SEQ ID NO 59
<211> LENGTH: 25
<212> TYPE: DNA
<213> ORGANISM: Homo sapiens

<400> SEQUENCE: 59
agagcgctgt aatgttgcag gatca                                     25

<210> SEQ ID NO 60
<211> LENGTH: 25
<212> TYPE: DNA
<213> ORGANISM: Homo sapiens

<400> SEQUENCE: 60
tgtttttcaa tgcccttcac aaggg                                     25

```
<210> SEQ ID NO 61
<211> LENGTH: 25
<212> TYPE: DNA
<213> ORGANISM: Homo sapiens

<400> SEQUENCE: 61
taaaaagtat ggagctgcta tggtg                                    25

<210> SEQ ID NO 62
<211> LENGTH: 25
<212> TYPE: DNA
<213> ORGANISM: Homo sapiens

<400> SEQUENCE: 62
gaccagacag taacatatgt ccttc                                    25

<210> SEQ ID NO 63
<211> LENGTH: 26
<212> TYPE: DNA
<213> ORGANISM: Homo sapiens

<400> SEQUENCE: 63
acattacagc gctctccaat gttaac                                   26

<210> SEQ ID NO 64
<211> LENGTH: 24
<212> TYPE: DNA
<213> ORGANISM: Homo sapiens

<400> SEQUENCE: 64
tgaggttgag aaatggcttg gacc                                     24

<210> SEQ ID NO 65
<211> LENGTH: 25
<212> TYPE: DNA
<213> ORGANISM: Homo sapiens

<400> SEQUENCE: 65
gccacagata tgttcttcct caatg                                    25

<210> SEQ ID NO 66
<211> LENGTH: 24
<212> TYPE: DNA
<213> ORGANISM: Homo sapiens

<400> SEQUENCE: 66
tgtggagagc acgtcttctc tgcc                                     24

<210> SEQ ID NO 67
<211> LENGTH: 50
<212> TYPE: PRT
<213> ORGANISM: Homo sapiens

<400> SEQUENCE: 67

Leu Ala Thr Val Lys Gly Asp Val His Asp Ile Gly Lys Asn Ile Val
  1               5                  10                  15

Gly Val Val Leu Gly Cys Asn Asn Phe Arg Val Ile Asp Leu Gly Val
             20                  25                  30

Met Thr Pro Cys Asp Lys Ile Leu Lys Ala Ala Leu Asp His Lys Ala
         35                  40                  45

Asp Ile
 50
```

```
<210> SEQ ID NO 68
<211> LENGTH: 50
<212> TYPE: PRT
<213> ORGANISM: Mus musculus

<400> SEQUENCE: 68

Leu Ala Thr Val Lys Gly Asp Val His Asp Ile Gly Lys Asn Ile Val
 1               5                  10                  15

Gly Val Val Leu Ala Cys Asn Asn Phe Arg Val Ile Asp Leu Gly Val
                20                  25                  30

Met Thr Pro Cys Asp Lys Ile Leu Gln Ala Ala Leu Asp His Lys Ala
         35                  40                  45

Asp Ile
     50

<210> SEQ ID NO 69
<211> LENGTH: 50
<212> TYPE: PRT
<213> ORGANISM: Cyanobacterium synechocystis

<400> SEQUENCE: 69

Ile Ala Thr Val Lys Gly Asp Val His Asp Ile Gly Lys Asn Leu Val
 1               5                  10                  15

Asp Ile Ile Leu Ser Asn Asn Gly Tyr Arg Val Val Asn Leu Gly Ile
                20                  25                  30

Lys Gln Pro Val Glu Asn Ile Ile Glu Ala Tyr Lys Lys His Arg Pro
         35                  40                  45

Asp Cys
     50

<210> SEQ ID NO 70
<211> LENGTH: 50
<212> TYPE: PRT
<213> ORGANISM: Mycobacterium leprae

<400> SEQUENCE: 70

Leu Ala Thr Val Lys Gly Asp Val His Asp Ile Gly Lys Asn Leu Val
 1               5                  10                  15

Asp Ile Ile Leu Ser Asn Asn Gly Tyr Glu Val Val Asn Leu Gly Ile
                20                  25                  30

Lys Gln Pro Ile Thr Asn Ile Leu Glu Val Ala Glu Asp Lys Ser Ala
         35                  40                  45

Asp Val
     50

<210> SEQ ID NO 71
<211> LENGTH: 50
<212> TYPE: PRT
<213> ORGANISM: Caenorrhabditis elegans

<400> SEQUENCE: 71

Ile Ala Thr Val Lys Gly Asp Val His Asp Ile Gly Lys Asn Ile Val
 1               5                  10                  15

Ser Val Val Leu Gly Cys Asn Asn Phe Lys Val Val Asp Leu Gly Val
                20                  25                  30

Met Thr Pro Cys Glu Asn Ile Ile Lys Ala Ala Ile Glu Glu Lys Ala
         35                  40                  45

Asp Phe
```

-continued

```
<210> SEQ ID NO 72
<211> LENGTH: 50
<212> TYPE: PRT
<213> ORGANISM: Hemophilus influenzae

<400> SEQUENCE: 72

Ile Ala Thr Val Lys Gly Asp Val His Asp Ile Gly Lys Asn Ile Val
  1               5                  10                  15

Ser Val Val Met Gln Cys Asn Asn Phe Glu Val Ile Asp Leu Gly Val
             20                  25                  30

Met Val Pro Ala Asp Lys Ile Ile Gln Thr Ala Ile Asn Gln Lys Thr
         35                  40                  45

Asp Ile
    50

<210> SEQ ID NO 73
<211> LENGTH: 50
<212> TYPE: PRT
<213> ORGANISM: Escherichia coli

<400> SEQUENCE: 73

Ile Ala Thr Val Lys Gly Asp Val His Asp Ile Gly Lys Asn Ile Val
  1               5                  10                  15

Gly Val Val Leu Gln Cys Asn Asn Tyr Glu Ile Val Asp Leu Gly Val
             20                  25                  30

Met Val Pro Ala Glu Lys Ile Leu Arg Thr Ala Lys Glu Val Asn Ala
         35                  40                  45

Asp Leu
    50

<210> SEQ ID NO 74
<211> LENGTH: 1265
<212> TYPE: PRT
<213> ORGANISM: Homo sapiens
<220> FEATURE:
<221> NAME/KEY: VARIANT
<222> LOCATION: (1)...(1265)
<223> OTHER INFORMATION: Xaa at position 881 is either Ile or no amino
      acid; Xaa at position 919 is either Asp or Gly; Xaa at position
      920 is either His or Asp.

<400> SEQUENCE: 74

Met Ser Pro Ala Leu Gln Asp Leu Ser Gln Pro Glu Gly Leu Lys Lys
  1               5                  10                  15

Thr Leu Arg Asp Glu Ile Asn Ala Ile Leu Gln Lys Arg Ile Met Val
             20                  25                  30

Leu Asp Gly Gly Met Gly Thr Met Ile Gln Arg Glu Lys Leu Asn Glu
         35                  40                  45

Glu His Phe Arg Gly Gln Glu Phe Lys Asp His Ala Arg Pro Leu Lys
     50                  55                  60

Gly Asn Asn Asp Ile Leu Ser Ile Thr Gln Pro Asp Val Ile Tyr Gln
 65                  70                  75                  80

Ile His Lys Glu Tyr Leu Leu Ala Gly Ala Asp Ile Ile Glu Thr Asn
                 85                  90                  95

Thr Phe Ser Ser Thr Ser Ile Ala Gln Ala Asp Tyr Gly Leu Glu His
                100                 105                 110

Leu Ala Tyr Arg Met Asn Met Cys Ser Ala Gly Val Ala Arg Lys Ala
            115                 120                 125
```

-continued

```
Ala Glu Glu Val Thr Leu Gln Thr Gly Ile Lys Arg Phe Val Ala Gly
        130                 135                 140
Ala Leu Gly Pro Thr Asn Lys Thr Leu Ser Val Ser Pro Ser Val Glu
145                 150                 155                 160
Arg Pro Asp Tyr Arg Asn Ile Thr Phe Asp Glu Leu Val Glu Ala Tyr
                165                 170                 175
Gln Glu Gln Ala Lys Gly Leu Leu Asp Gly Val Asp Ile Leu Leu
                180                 185                 190
Ile Glu Thr Ile Phe Asp Thr Ala Asn Ala Lys Ala Ala Leu Phe Ala
            195                 200                 205
Leu Gln Asn Leu Phe Glu Glu Lys Tyr Ala Pro Arg Pro Ile Phe Ile
    210                 215                 220
Ser Gly Thr Ile Val Asp Lys Ser Gly Arg Thr Leu Ser Gly Gln Thr
225                 230                 235                 240
Gly Glu Gly Phe Val Ile Ser Val Ser His Gly Glu Pro Leu Cys Ile
                245                 250                 255
Gly Leu Asn Cys Ala Leu Gly Ala Ala Glu Met Arg Pro Phe Ile Glu
            260                 265                 270
Ile Ile Gly Lys Cys Thr Thr Ala Tyr Val Leu Cys Tyr Pro Asn Ala
        275                 280                 285
Gly Leu Pro Asn Thr Phe Gly Asp Tyr Asp Glu Thr Pro Ser Met Met
    290                 295                 300
Ala Lys His Leu Lys Asp Phe Ala Met Asp Gly Leu Val Asn Ile Val
305                 310                 315                 320
Gly Gly Cys Cys Gly Ser Thr Pro Asp His Ile Arg Glu Ile Ala Glu
                325                 330                 335
Ala Val Lys Asn Cys Lys Pro Arg Val Pro Pro Ala Thr Ala Phe Glu
            340                 345                 350
Gly His Met Leu Leu Ser Gly Leu Glu Pro Phe Arg Ile Gly Pro Tyr
        355                 360                 365
Thr Asn Phe Val Asn Ile Gly Glu Arg Cys Asn Val Ala Gly Ser Arg
    370                 375                 380
Lys Phe Ala Lys Leu Ile Met Ala Gly Asn Tyr Glu Glu Ala Leu Cys
385                 390                 395                 400
Val Ala Lys Val Gln Val Glu Met Gly Ala Gln Val Leu Asp Val Asn
                405                 410                 415
Met Asp Asp Gly Met Leu Asp Gly Pro Ser Ala Met Thr Arg Phe Cys
            420                 425                 430
Asn Leu Ile Ala Ser Glu Pro Asp Ile Ala Lys Val Pro Leu Cys Ile
        435                 440                 445
Asp Ser Ser Asn Phe Ala Val Ile Glu Ala Gly Leu Lys Cys Cys Gln
    450                 455                 460
Gly Lys Cys Ile Val Asn Ser Ile Ser Leu Lys Glu Gly Glu Asp Asp
465                 470                 475                 480
Phe Leu Glu Lys Ala Arg Lys Ile Lys Lys Tyr Gly Ala Ala Met Val
                485                 490                 495
Val Met Ala Phe Asp Glu Glu Gly Gln Ala Thr Glu Thr Asp Thr Lys
            500                 505                 510
Ile Arg Val Cys Thr Arg Ala Tyr His Leu Leu Val Lys Lys Leu Gly
        515                 520                 525
Phe Asn Pro Asn Asp Ile Ile Phe Asp Pro Asn Ile Leu Thr Ile Gly
    530                 535                 540
```

-continued

```
Thr Gly Met Glu Glu His Asn Leu Tyr Ala Ile Asn Phe Ile His Ala
545                 550                 555                 560

Thr Lys Val Ile Lys Glu Thr Leu Pro Gly Ala Arg Ile Ser Gly Gly
                565                 570                 575

Leu Ser Asn Leu Ser Phe Ser Phe Arg Gly Met Glu Ala Ile Arg Glu
                580                 585                 590

Ala Met His Gly Val Phe Leu Tyr His Ala Ile Lys Ser Gly Met Asp
            595                 600                 605

Met Glu Ile Val Asn Ala Gly Asn Leu Pro Val Tyr Asp Asp Ile His
        610                 615                 620

Lys Glu Leu Leu Gln Leu Cys Glu Asp Leu Ile Trp Asn Lys Asp Pro
625                 630                 635                 640

Glu Ala Thr Glu Lys Leu Leu Arg Tyr Ala Gln Thr Gln Gly Thr Gly
                645                 650                 655

Gly Lys Lys Val Ile Gln Thr Asp Glu Trp Arg Asn Gly Pro Val Glu
                660                 665                 670

Glu Arg Leu Glu Tyr Ala Leu Val Lys Gly Ile Glu Lys His Ile Ile
            675                 680                 685

Glu Asp Thr Glu Glu Ala Arg Leu Asn Gln Lys Lys Tyr Pro Arg Pro
        690                 695                 700

Leu Asn Ile Ile Glu Gly Pro Leu Met Asn Gly Met Lys Ile Val Gly
705                 710                 715                 720

Asp Leu Phe Gly Ala Gly Lys Met Phe Leu Pro Gln Val Ile Lys Ser
                725                 730                 735

Ala Arg Val Met Lys Lys Ala Val Gly His Leu Ile Pro Phe Met Glu
                740                 745                 750

Lys Glu Arg Glu Glu Thr Arg Val Leu Asn Gly Thr Val Glu Glu Glu
            755                 760                 765

Asp Pro Tyr Gln Gly Thr Ile Val Leu Ala Thr Val Lys Gly Asp Val
        770                 775                 780

His Asp Ile Gly Lys Asn Ile Val Gly Val Leu Gly Cys Asn Asn
785                 790                 795                 800

Phe Arg Val Ile Asp Leu Gly Val Met Thr Pro Cys Asp Lys Ile Leu
                805                 810                 815

Lys Ala Ala Leu Asp His Lys Ala Asp Ile Ile Gly Leu Ser Gly Leu
                820                 825                 830

Ile Thr Pro Ser Leu Asp Glu Met Ile Phe Val Ala Lys Glu Met Glu
            835                 840                 845

Arg Leu Ala Ile Arg Ile Pro Leu Leu Ile Gly Gly Ala Thr Thr Ser
        850                 855                 860

Lys Thr His Thr Ala Val Lys Ile Ala Pro Arg Tyr Ser Ala Pro Val
865                 870                 875                 880

Xaa His Val Leu Asp Ala Ser Lys Ser Val Val Cys Ser Gln Leu
                885                 890                 895

Leu Asp Glu Asn Leu Lys Asp Glu Tyr Phe Glu Glu Ile Met Glu Glu
                900                 905                 910

Tyr Glu Asp Ile Arg Gln Xaa Xaa Tyr Glu Ser Leu Lys Glu Arg Arg
            915                 920                 925

Tyr Leu Pro Leu Ser Gln Ala Arg Lys Ser Gly Phe Gln Met Asp Trp
        930                 935                 940

Leu Ser Glu Pro His Pro Val Lys Pro Thr Phe Ile Gly Thr Gln Val
945                 950                 955                 960

Phe Glu Asp Tyr Asp Leu Gln Lys Leu Val Asp Tyr Ile Asp Trp Lys
```

```
                     965                 970                 975
Pro Phe Phe Asp Val Trp Gln Leu Arg Gly Lys Tyr Pro Asn Arg Gly
                980                 985                 990
Phe Pro Lys Ile Phe Asn Asp Lys Thr Val Gly Gly Glu Ala Arg Lys
            995                 1000                1005
Val Tyr Asp Asp Ala His Asn Met Leu Asn Thr Leu Ile Ser Gln Lys
        1010                1015                1020
Lys Leu Arg Ala Arg Gly Val Val Gly Phe Trp Pro Ala Gln Ser Ile
1025                1030                1035                1040
Gln Asp Asp Ile His Leu Tyr Ala Glu Ala Val Pro Gln Ala Ala
                1045                1050                1055
Glu Pro Ile Ala Thr Phe Tyr Gly Leu Arg Gln Gln Ala Glu Lys Asp
            1060                1065                1070
Ser Ala Ser Thr Glu Pro Tyr Tyr Cys Leu Ser Asp Phe Ile Ala Pro
        1075                1080                1085
Leu His Ser Gly Ile Arg Asp Tyr Leu Gly Leu Phe Ala Val Ala Cys
    1090                1095                1100
Phe Gly Val Glu Glu Leu Ser Lys Ala Tyr Glu Asp Asp Gly Asp Asp
1105                1110                1115                1120
Tyr Ser Ser Ile Met Val Lys Ala Leu Gly Asp Arg Leu Ala Glu Ala
                1125                1130                1135
Phe Ala Glu Glu Leu His Glu Arg Val Arg Arg Glu Leu Trp Ala Tyr
            1140                1145                1150
Cys Gly Ser Glu Gln Leu Asp Val Ala Asp Leu Arg Arg Leu Arg Tyr
        1155                1160                1165
Lys Gly Ile Arg Pro Ala Pro Gly Tyr Pro Ser Gln Pro Asp His Thr
    1170                1175                1180
Glu Lys Leu Thr Met Trp Arg Leu Ala Asp Ile Glu Gln Ser Thr Gly
1185                1190                1195                1200
Ile Arg Leu Thr Glu Ser Leu Ala Met Ala Pro Ala Ser Ala Val Ser
                1205                1210                1215
Gly Leu Tyr Phe Ser Asn Leu Lys Ser Lys Tyr Phe Ala Val Gly Lys
            1220                1225                1230
Ile Ser Lys Asp Gln Val Glu Asp Tyr Ala Leu Arg Lys Asn Ile Ser
        1235                1240                1245
Val Ala Glu Val Glu Lys Trp Leu Gly Pro Ile Leu Gly Tyr Asp Thr
    1250                1255                1260
Asp
1265

<210> SEQ ID NO 75
<211> LENGTH: 3856
<212> TYPE: DNA
<213> ORGANISM: Homo sapiens
<220> FEATURE:
<221> NAME/KEY: variation
<222> LOCATION: (1)...(3856)
<223> OTHER INFORMATION: nnn at positions 2640-2642 is either AAT or no
      nucleotides; n at position 2756 is either A or G; n at position
      2758 is either C or G.

<400> SEQUENCE: 75
atgtcacccg cgctccaaga cctgtcgcaa cccgaaggtc tgaagaaaac cctgcgggat      60
gagatcaatg ccattctgca agagaggatt atggtgctgg atggagggat ggggaccatg     120
atccagcggg agaagctaaa cgaagaacac ttccgaggtc aggaatttaa agatcatgcc     180
```

-continued

| | |
|---|---|
| aggccgctga aaggcaacaa tgacatttta agtataactc agcctgatgt catttaccaa | 240 |
| atccataagg aatacttgct ggctggggca gatatcattg aaacaaatac ttttagcagc | 300 |
| actagtattg cccaagctga ctatggcctt gaacacttgg cctaccggat gaacatgtgc | 360 |
| tctgcaggag tggccagaaa agctgccgag gaggtaactc tccagacagg aattaagagg | 420 |
| tttgtggcag gggctctggg tccgactaat aagacactct ctgtgtcccc atctgtggaa | 480 |
| aggccggatt ataggaacat cacatttgat gagcttgttg aagcatacca agagcaggcc | 540 |
| aaaggacttc tggatggcgg ggttgatatc ttactcattg aaactatttt tgatactgcc | 600 |
| aatgccaagg cagccttgtt tgcactccaa atctttttg aggagaaata tgctccccgg | 660 |
| cctatcttta tttcagggac gatcgttgat aaaagtgggc ggactctttc cggacagaca | 720 |
| ggagagggat ttgtcatcag cgtgtctcat ggagaaccac tctgcattgg attaaattgt | 780 |
| gctttgggtg cagctgagat gagacctttt attgaaataa ttggaaaatg tacaacagcc | 840 |
| tatgtcctct gttatcccaa tgcaggtctt cccaacacct tggtgacta tgatgaaacg | 900 |
| ccttctatga tggccaagca cctaaaggat tttgctatgg atggcttggt caatatagtt | 960 |
| ggaggatgct gtgggtcaac accagatcat atcagggaaa ttgctgaagc tgtgaaaaat | 1020 |
| tgtaagccta gagttccacc tgccactgct tttgaaggac atatgttact gtctggtcta | 1080 |
| gagcccttca ggattggacc gtacaccaac tttgttaaca ttggagagcg ctgtaatgtt | 1140 |
| gcaggatcaa ggaagtttgc taaactcatc atgcaggaa actatgaaga agccttgtgt | 1200 |
| gttgccaaag tgcaggtgga atgggagcc caggtgttgg atgtcaacat ggatgatggc | 1260 |
| atgctagatg gtccaagtgc aatgaccaga ttttgcaact taattgcttc gagccagac | 1320 |
| atcgcaaagg tacctttgtg catcgactcc tccaatttg ctgtgattga agctgggtta | 1380 |
| aagtgctgcc aagggaagtg cattgtcaat agcattagtc tgaaggaagg agaggacgac | 1440 |
| ttcttggaga aggccaggaa gattaaaaag tatggagctg ctatggtggt catggctttt | 1500 |
| gatgaagaag gacaggcaac agaaacagac acaaaaatca gagtgtgcac ccgggcctac | 1560 |
| catctgcttg tgaaaaaact gggctttaat ccaaatgaca ttattttga ccctaatatc | 1620 |
| ctaaccattg ggactggaat ggaggaacac aacttgtatg ccattaatt tatccatgca | 1680 |
| acaaaagtca ttaaagaaac attacctgga gccagaataa gtggaggtct ttccaacttg | 1740 |
| tccttctcct tccgaggaat ggaagccatt cgagaagcaa tgcatggggt tttcctttac | 1800 |
| catgcaatca agtctggcat ggacatggag atagtgaatg ctggaaacct ccctgtgtat | 1860 |
| gatgatatcc ataaggaact tctgcagctc tgtgaagatc tcatctggaa taagacccct | 1920 |
| gaggccactg agaagctctt acgttatgcc cagactcaag gcacaggagg gaagaaagtc | 1980 |
| attcagactg atgagtggag aaatggccct gtcgaagaac gccttgagta tgcccttgtg | 2040 |
| aagggcattg aaaacatat tattgaggat actgaggaag ccaggttaaa ccaaaaaaaa | 2100 |
| tatccccgac ctctcaatat aattgaagga cccctgatga atggaatgaa aattgttggt | 2160 |
| gatcttttg gagctggaaa atgtttcta cctcaggtta taaagtcagc ccgggttatg | 2220 |
| aagaaggctg ttgccacct tatccctttc atggaaaaag aagagaaga accagagtg | 2280 |
| cttaacggca cagtagaaga agaggaccct taccagggca ccatcgtgct ggccactgtt | 2340 |
| aaaggcgacg tgcacgacat aggcaagaac atagttggag tagtccttgg ctgcaataat | 2400 |
| ttccagagtta ttgatttagg agtcatgact ccatgtgata agatactgaa agctgctctt | 2460 |
| gaccacaaag cagatataat tggcctgtca ggactcatca ctccttccct ggatgaaatg | 2520 |
| atttttgttg ccaaggaaat ggagagatta gctataagga ttccattgtt gattggagga | 2580 |

```
gcaaccactt caaaaaccca cacagcagtt aaaatagctc cgagatacag tgcacctgtn    2640
nnccatgtcc tggacgcgtc caagagtgtg gtggtgtgtt cccagctgtt agatgaaaat    2700
ctaaaggatg aatactttga ggaaatcatg gaagaatatg aagatattag acaggncnat    2760
tatgagtctc tcaaggagag gagatactta cccttaagtc aagccagaaa aagtggtttc    2820
caaatggatt ggctgtctga acctcaccca gtgaagccca cgtttattgg gacccaggtc    2880
tttgaagact atgacctgca gaagctggtg gactacattg actggaagcc tttctttgat    2940
gtctggcagc tccggggcaa gtacccgaat cgaggcttcc ccaagatatt taacgacaaa    3000
acagtaggtg gagaggccag gaaggtctac gatgatgccc acaatatgct gaacacactg    3060
attagtcaaa agaaactccg ggcccggggt gtggttgggt tctggccagc acagagtatc    3120
caagacgaca ttcacctgta cgcagaggct gctgtgcccc aggctgcaga gcccatagcc    3180
actttctatg ggttaaggca acaggctgag aaggactctg ccagcacgga gccatactac    3240
tgcctctcag acttcatcgc tcccttgcat tctggcatcc gtgactacct gggcctgttt    3300
gccgttgcct gctttggggt agaagagctg agcaaggcct atgaggatga tggtgacgac    3360
tacagcagca tcatggtcaa ggcgctgggg gaccggctgg cagaggcctt tgcagaagag    3420
ctccatgaaa gagttcgccg agaactgtgg gcctactgtg gcagtgagca gctggacgtc    3480
gcagacctgc gaaggttgcg gtacaagggc atccgcccgg ctcctggcta ccccagccag    3540
cccgaccaca ccgagaagct caccatgtgg agactcgcag acatcgagca gtctacaggc    3600
attaggttaa cagaatcatt agcaatggca cctgcttcag cagtctcagg cctctacttc    3660
tccaatttga agtccaaata ttttgctgtg gggaagattt ccaaggatca ggttgaggat    3720
tatgcattga ggaagaacat atctgtggct gaggttgaga aatggcttgg acccattttg    3780
ggatatgata cagactaact ttttttttttt tttttgcctt ttttatcttg atgatcctca    3840
aggaaataca acctag                                                    3856

<210> SEQ ID NO 76
<211> LENGTH: 10
<212> TYPE: DNA
<213> ORGANISM: Homo sapiens

<400> SEQUENCE: 76
gacaacatgt                                                             10
```